United States Patent [19]
Williams et al.

[11] Patent Number: 6,153,745
[45] Date of Patent: Nov. 28, 2000

[54] RELATING TO MUTAGENESIS OF NUCLEIC ACIDS

[75] Inventors: David Williams, Sheffield; Daniel Brown, Cambridge; Manuella Carla Zaccolo, Cambridge; Ermanno Gherardi, Cambridge, all of United Kingdom

[73] Assignee: Amersham Pharmacia Biotech UK Limited, Buckinghamshire, United Kingdom

[21] Appl. No.: 09/043,514

[22] PCT Filed: Sep. 19, 1996

[86] PCT No.: PCT/GB96/02333

§ 371 Date: Jul. 6, 1998

§ 102(e) Date: Jul. 6, 1998

[87] PCT Pub. No.: WO97/11083

PCT Pub. Date: Mar. 27, 1997

[30] Foreign Application Priority Data

Sep. 22, 1995 [GB] United Kingdom .................... 9519425
Feb. 1, 1996 [GB] United Kingdom .................... 9602011

[51] Int. Cl.[7] .......................... C07H 21/02; C07H 21/04; C12P 19/34
[52] U.S. Cl. ..................................... 536/25.32; 536/26.23; 536/26.26; 435/91.2; 435/91.1
[58] Field of Search .............................. 536/25.32, 26.23, 536/26.26; 435/91.1, 91.2

[56] References Cited

U.S. PATENT DOCUMENTS 5,434,257  7/1995  Matteucci et al. ..................... 536/24.3

FOREIGN PATENT DOCUMENTS

| 9514523 | 10/1996 | Germany . |
| 9616425 | 9/1995 | United Kingdom . |
| 9605011 | 2/1996 | United Kingdom . |
| 9507918 | 3/1995 | WIPO . |
| 9511911 | 5/1995 | WIPO . |
| 9711083 | 3/1997 | WIPO . |
| 9803673 | 1/1998 | WIPO . |

OTHER PUBLICATIONS

Brown et al., "Synthesis and Duplex Stability of Oligonucleotides Containing Adenine–Guanine Analogues," *Carbohydrate Research*, 216, 129–139 (Sep. 2, 1991).

Thoo–Lin et al.(I), "Synthesis and Duplex Stability of Oligonucleotides Containing Cytosine–Thymine Analogues," *Nucleic Acids Research*, 17(24), 10373–10383 (Dec. 25, 1989).

Nedderman et al.(I), "Base Pairing of Cytosine Analogues with Adenine and Guanine in Oligonucleotide Duplexes: Evidence for Exchange Between Watson–Crick and Wibble Base Pair Using $^1$H NME Spectroscopy," *J. Chemical Society, Chemical Communications*, (Issue No. 18), 1357–1359 (Oct. 1991).

Loakes et al., "The Synthesis of Bicyclic $N^4$–Amino–2'–deoxycytidine Derivatives," *Nucleosides and Nucleotides,*14(3–5), 1057–1059 (May–Jul. 1995).

Van Meervelt et al., "To Wobble or Not to Wobble: Modified Bases Incorporated into DNA," *Nucleosides and Nucleotides*, 14(3–5), 1057–1059 (May–Jul. 1995).

Nedderman et al.,(i), "Molecular Basis for Methoxyamine–Initiated Mutagenesis: Proton Nuclear Magnetic Resonance Studies of Oligonucleotide Duplexes Containing Base–Modified Cystosine Residues," *J. Molecular Biology*, 230(3), 1068–1076 (1993); *Chem. Abstr.*, 119(5), p. 320, Abstr. No. 43094b (Aug. 2, 1993); only Abstract supplied.

Thoo–Lin et al.(II), "Synthesis of Oligodeoxyribonucleotides Containing Degenerate Bases and Their Use as Primers in the Polymerase Chain Reaction," *Nucleic Acids Research*, 20(19), 5149–5152 (Oct. 11, 1992).

(List continued on next page.)

*Primary Examiner*—L. Eric Crane
*Attorney, Agent, or Firm*—Pillsbury Madison & Sutro, LLP

[57] ABSTRACT

The invention concerns novel compounds having defined structural formulae and methods of mutating a nucleic acid sequence, the method comprising replicating a template sequence in the presence of a nucleoside triphosphate analogue in accordance with the invention, so as to form non-identical copies of the template sequence comprising one or more nucleoside triphosphate analogue residues, and a kit for use in performing the method of the invention.

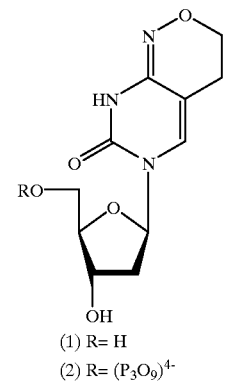

(1) R = H
(2) R = $(P_3O_9)^{4-}$

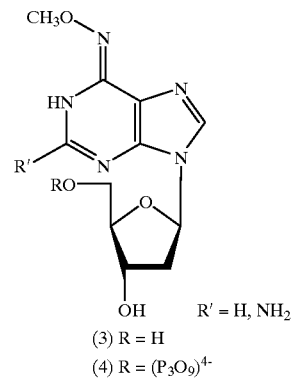

R' = H, NH$_2$
(3) R = H
(4) R = $(P_3O_9)^{4-}$

18 Claims, 33 Drawing Sheets

OTHER PUBLICATIONS

Abdul–Masih et al., "Biochemical Studies on the Mutagen, 6–N–Hydroxylaminopurine," *J. Biological Chemistry,* 261, 2020–2026 (Feb. 15, 1966).

Abdul–Masih, "Biochemical Studies ont he Synthesis of 6–N–Hydroxypurine Deoxynucleoside Triphosphate and Its Incorporation Into Deoxyribonucleic Acid," University Microfilms Document No. 8518469, 1985, Ph.D Dissertation (John Hopkins University, Baltimore MD, University Microfilms International, Ann Arbor, MI.

Budowsky et al.(I), "Mechanism of Mutagenic Action of Hydroxylamine. II. Reaction of Hydroxylamine with the Adenine Nucleus," *J. Molecular Biology,* 44, 205–207 (Sep. 28, 1969).

Singer et al., "Reaction of O–Methylhydroxylamine with Adenosine Shifts Tautomeric Equilibrium to Cause Transitions," *FEBS Letters,* 139(1), 69–71 (Mar. 8, 1982).

Budowsky et al.(II), "Mechanism of Mutagenic Action of Hydroxylamine. VIII. Functional Properties of the Modified Adenosine Residues," *Biochimica et Biophysica Acta,* 390(1), 1–13 (April 16, 1975).

Janion, "The Synthesis and Properties of $N^6$–Substituted 2–Amino purine Derivatives," *Acta Biochimica Polonica,* 23(1), 57–67 (1976).

Nakao et al.(Takeda Chemical Industries), "6–Hydroxylaminopurine Ribotides by Bacterial Fermentation," Japanese Patent Publication 72 08 587, Sep. 21, 1968; *Chem. Abstr.,* 77(5), p. 376, Abstr. No. 32695m (Jul. 31, 1972); only Abstract supplied.

Donaldson et al., "Synthetic and Regulatory Properties of an Adenosine 5'–Phosphate Analog, $N^6$–Methoxyadenosine 5'–Phosphate," *Biochimica et Biophysica Acta,* 184(3), 655–657 (1969†); *Chem. Abstr.,* 71(19), p. 168, Abstr. No. 89293j (Nov. 10, 1969); only Abstract supplied.

Tindall et al., "Fidelity of DNA Synthesis by the *Thermus aquaticus* DNA Polymerase," *Biochemistry,* 27(16), 6008–6013 (Aug. 9, 1988).

Zaccolo et al., "An Approach to Random Mutagenesis of DNA Using Mixtures of Triphosphate Derivatives on Nucleoside Analogues," *J. Molecular Biology,* 255, 589–603 (1996†).

Moore et al., "Direct Observation of Two Base Pairing Modes of a Cytosine–Thymine Analogue with Guanine in a DNA Z–form Duplex: Significance for Base Analogue Mutagenesis," *Journal of Molecular Biology,* 251(1), 665–673 (Sep. 1, 1995).

(1) R = H
(2) R = (P₃O₉)⁴⁻

(3) R = H
(4) R = (P₃O₉)⁴⁻
R' = H, NH₂

R' = H, NH₂
(5)

(6) X = O, S, N–alkyl

P-imino-A

P-amino-G wobble P-imino-G

```
       1                    23
5'-d(GGCCTTGATATTCACAAACGAAT)              3' PRIMER

3'-d(CCGGAACTATAAGTGTTTGCTT ACCATTCT)      5' TEMPLATE 1 (dPTP/dTTP)
                            123

3'-d(CCGGAACTATAAGTGTTTGCTT ACCGTTCT)      5' TEMPLATE 2 (dPTP/dCTP)
```

Fig. 7A dPTP

| from \ to | G | A | T | C |
|---|---|---|---|---|
| G | — | 9.2 | 0 | 0 |
| A | 46.6 | — | 0.5 | 0 |
| T | 0.2 | 0 | — | 35.5 |
| C | 0 | 0 | 8.0 | — |

Fig. 7B 8-oxodGTP

| from \ to | G | A | T | C |
|---|---|---|---|---|
| G | — | 1.1 | 0 | 0 |
| A | 0 | — | 0 | 38.8 |
| T | 59 | 0 | — | 0 |
| C | 0 | 1.1 | 0 | — |

Fig. 7C dPTP+8-oxodGTP

| from \ to | G | A | T | C |
|---|---|---|---|---|
| G | — | 7.8 | 0 | 0 |
| A | 40.7 | — | 0.2 | 6.6 |
| T | 1.8 | 0 | — | 37.6 |
| C | 0.7 | 0 | 5.4 | — |

← Fig. 8A   Fig. 8D ↓

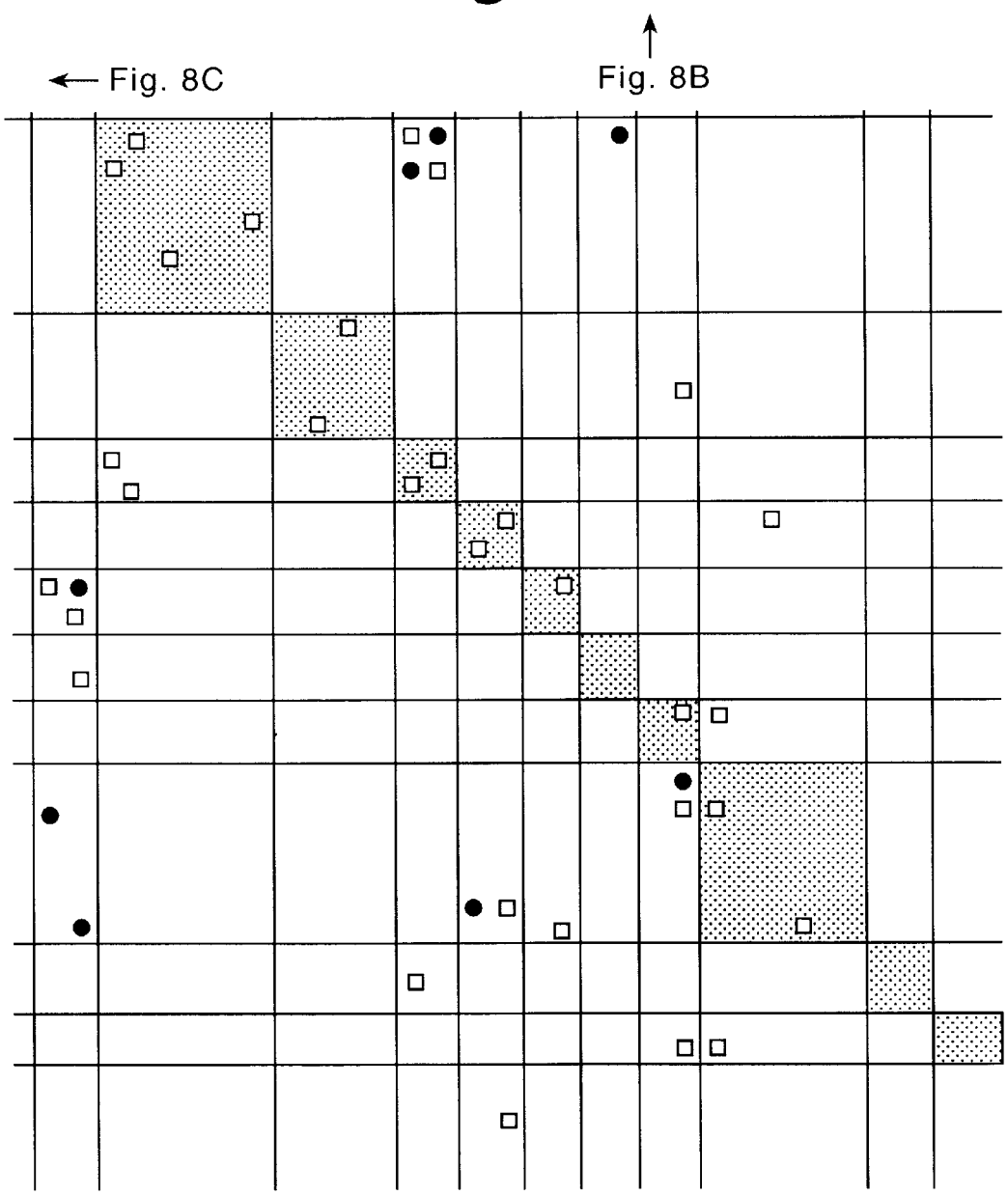

|     |     |   |   |   |   |   |   |   |   |   |
|-----|-----|---|---|---|---|---|---|---|---|---|
| Tyr | TAC |   |   |   |   |   |   |   |   | ▒ |
|     | TAT |   |   |   |   |   |   |   |   | ▒ |
| Ser | AGC |   |   |   |   |   |   |   |   |   |
|     | AGT |   |   |   |   |   |   |   |   |   |
|     | TCA |   |   |   |   |   |   |   |   |   |
|     | TCC |   |   |   |   |   |   |   |   |   |
|     | TCG |   |   |   |   |   |   |   |   |   |
|     | TCT |   |   |   |   |   |   |   |   | □□ |
| Thr | ACA |   |   |   |   |   |   |   |   |   |
|     | ACC |   |   |   |   |   |   |   |   |   |
|     | ACG |   |   |   |   |   |   |   |   |   |
|     | ACT |   |   |   |   |   |   |   |   |   |
| Asn | AAC |   |   |   |   |   |   |   |   |   |
|     | AAT |   |   |   |   |   |   |   |   |   |
| Gln | CAA |   |   |   |   |   |   |   |   |   |
|     | CAG |   |   |   |   |   |   |   |   |   |
| Cys | TGC |   |   |   |   |   |   |   |   |   |
|     | TGT |   |   |   |   |   |   |   |   |   |
| His | CAC |   |   |   |   |   |   |   |   |   |
|     | CAT |   |   |   |   |   |   |   |   |   |
| Lys | AAA |   |   |   |   |   |   |   |   |   |
|     | AAG |   |   |   |   |   |   |   |   |   |
| Arg | AGA |   |   |   |   |   |   |   |   |   |
|     | AGG |   |   |   |   |   | □ |   |   |   |
|     | CGA |   |   |   |   |   |   |   |   |   |
|     | CGC |   |   | □ |   |   |   |   |   |   |
|     | CGG |   |   |   | □ |   |   |   |   |   |
|     | CGT |   |   |   |   |   |   |   |   |   |
| Glu | GAC |   |   |   |   |   |   |   |   |   |
|     | GAT |   |   |   |   |   |   |   |   | □ |
| Asp | GAA |   |   |   |   |   |   |   |   |   |
|     | GAG |   |   |   |   |   |   |   |   |   |
| ochre | TAA |   |   |   |   |   |   |   |   |   |
| amber | TAG |   |   |   |   |   |   |   |   | □ |
| opal | TGA |   |   |   |   |   |   |   |   |   |

← Fig. 9C    Fig. 9B ↑

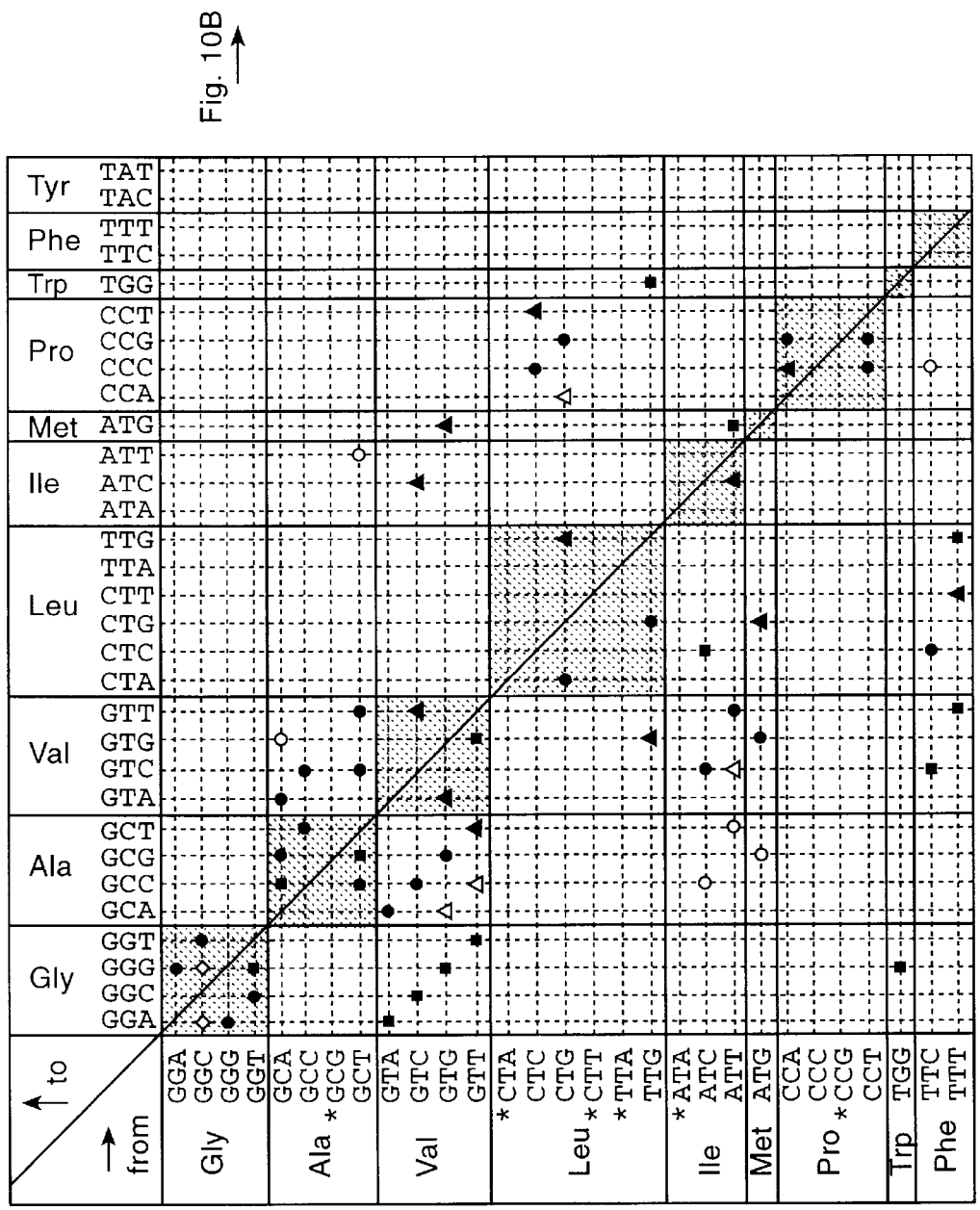

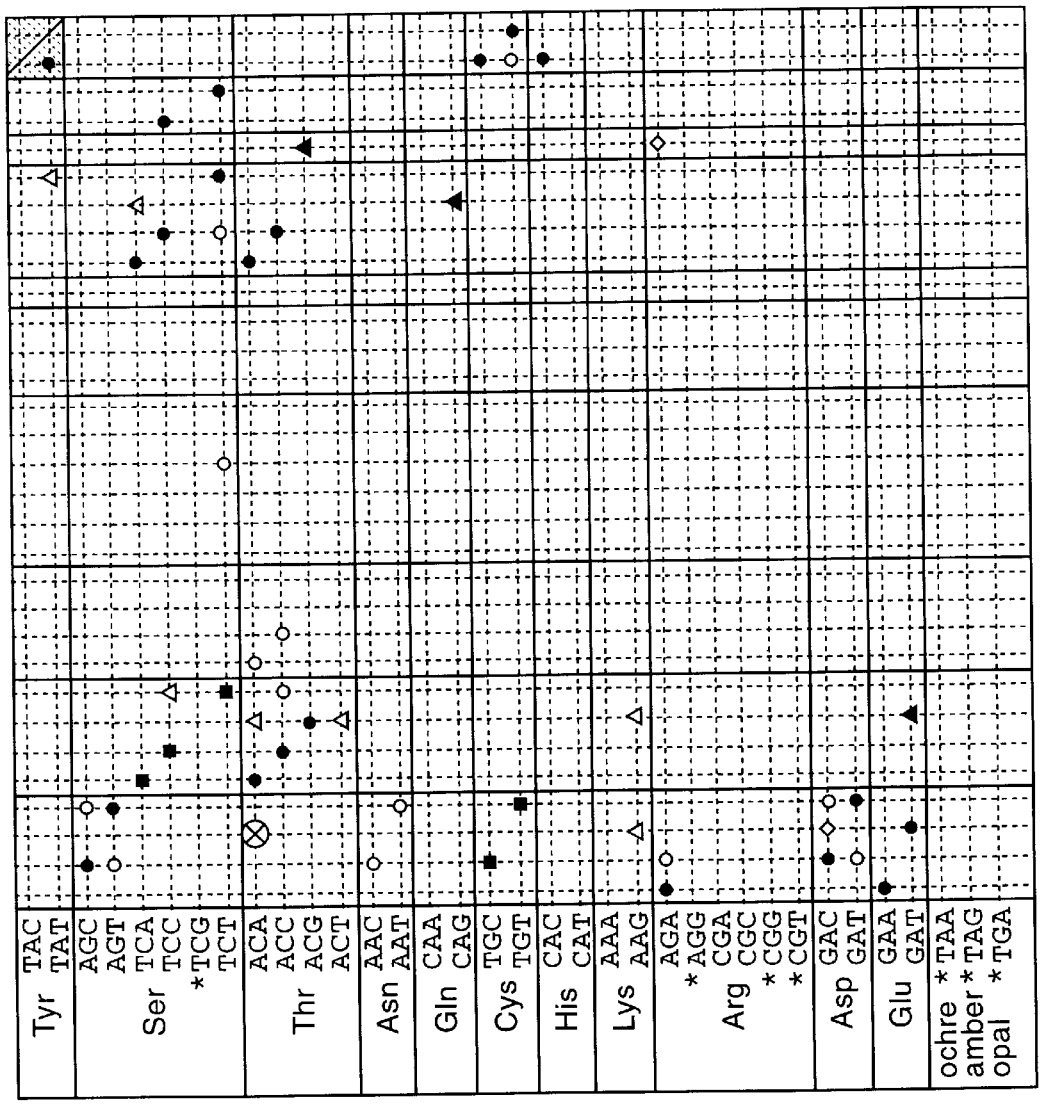

Fig. 11A1

|  |  |  |  |  | +10 |  |  |  |  |  |  |  |  |  | +20 |  |  |  |  |  |
|---|---|---|---|---|---|---|---|---|---|---|---|---|---|---|---|---|---|---|---|---|---|
| A | E | S | G | G | L | I | Q | P | G | G | S | L | R | L | S | C | A | A | S | G | F |
| 22 | GAG | TCT | GGA | GGC | TTG | ATC | CAG | CCT | GGG | GGG | TCC | CTG | AGA | CTC | TCC | TGT | GCA | GCC | TCT | GGG | TTC |
| P1.1 | --- | --- | --- | --- | --- | --- | --- | --- | --- | --- | --- | --- | --- | --- | --- | --- | --- | --- | --- | --- | --- |
| P1.2 | --- | --- | --- | --- | --- | --- | --- | --- | --- | --- | --- | --- | --- | --- | --- | --- | --- | --- | --- | --- | --- |
| P1.3 | --- | --- | --- | --- | --- | --- | --- | --- | --- | --- | --- | --- | --- | --- | --- | --- | --- | --- | --- | --- | --- |
| P5.2 | --- | --- | --- | --- | --- | --- | --- | --- | --- | --- | P C-- | --- | --- | --- | --- | --- | --- | --- | --- | --- | --- |
| P5.3 | --- | --- | --- | --- | --- | --- | --- | --- | --- | --- | --- | --- | -G- | --- | --- | -C- | --- | --- | -C- | --- | --- |
| P10.1 | --- | --- | --- | --- | C-- S | --- | --- | --- | --- | --- | P C-- | --- | --- | --- | --- | --- | --- | --- | --- | --- | S -C- |
| P10.3 | --- | --- | --- | --- | -C- | V G-- | * T-- | --- | --- | --- | P C-- | --- | --- | P -C- | P C-- | --- | --- | --- | --- | --- | --- |
| P18.1 | --- | --- | --- | --- | C-- | --- | A -A- | A --A | --- | --- | --- | --- | --- | --- | --- | --- | --- | -T- | --- | --- | --- |
| P30.2 | --- | --- | --- | --- | --- | --- | --- | --- | --- | --- | --- | --- | --- | --- | --- | P C-- | T A-G | --- | --- | --- | S -C- |
| P30.3 | --- | --- | --- | --- | --- | --- | --- | -C- | --- | --- | --- | --- | G G-G | --- | --- | Y -AC | --- | --- | --- | --- | P CC- |
| P30.4 | --- | --- | --- | --- | --- | --- | --- | --- | --- | --- | --- | --- | --- | --- | P C-- | V -T- | V T-- | --- | --- | --- | --- |
| P30.6 | --- | --- | --- | --- | --- | --- | --- | -G- | --- | --- | --- | --- | --- | --- | --- | --- | --- | --- | --- | --- | --- |

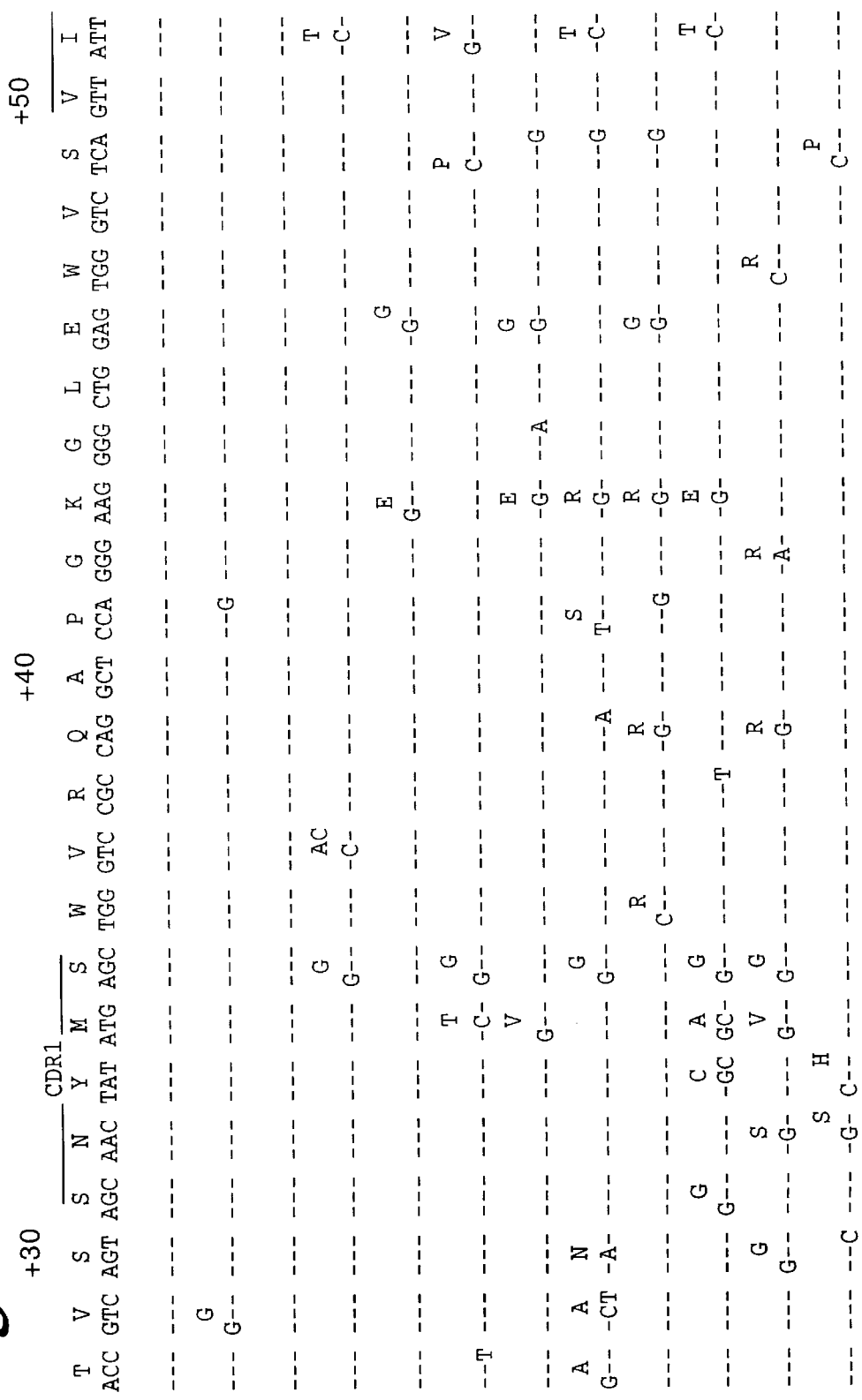
Fig. 11A2

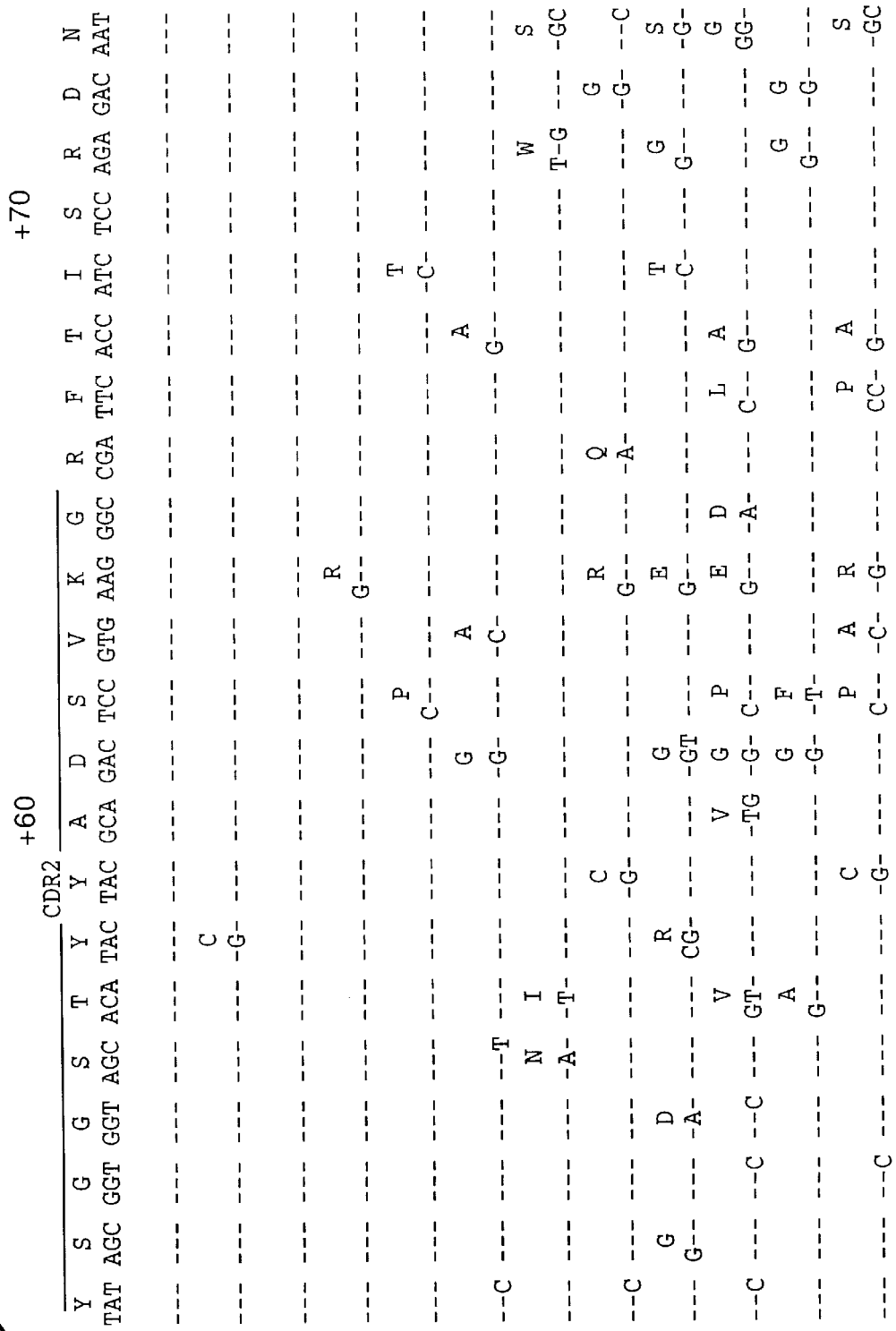
Fig. 11A3

|  |  | E | S | G | G | G | L +10 | I | Q | P | G | G | S | L | R | L +20 | S | C | A |
|---|---|---|---|---|---|---|---|---|---|---|---|---|---|---|---|---|---|---|---|
|  |  | GAG | TCT | GGA | GGA | GGC | TTG | ATC | CAG | CCT | GGG | GGG | TCC | CTG | AGA | CTC | TCC | TGT | GCA |
| 22 |  | --- | --- | --- | --- | --- | --- | --- | --- | --- | --- | --- | --- | --- | --- | --- | --- | --- | --- |
| G12.1 |  | --- | --- | --- | --- | --- | --- | --- | --- | --- | --- | --- | --- | --- | --- | --- | --- | --- | --- |
| G12.2 |  | --- | --- | --- | --- | --- | --- | --- | --- | --- | --- | --- | --- | --- | --- | --- | --- | --- | --- |
| G12.3 |  | --- | --- | --- | --- | --- | --- | --- | --- | --- | --- | --- | --- | --- | --- | --- | --- | --C | --- |
| G12.6 |  | --- | --- | --- | --- | --- | --- | --- | --- | --- | --- | --- | --- | --- | --- | --- | --- | --- | --- |
| G18.2 |  | --- | --- | --- | --- | --- | --- | --- | --- | --- | --- | --- | --- | --- | --- | --- | --- | --- | --- |
| G18.3 |  | --- | --- | --- | --- | --- | --- | --- | --- | --- | --- | --- | --- | --- | --- | --- | --- | --- | --- |
| G18.4 |  | --- | --- | --- | --- | --- | --- | --- | --- | --- | --- | --- | --- | --- | --- | --- | --- | --- | --- |
| G18.5 |  | --- | --- | --- | --- | --- | --- | V<br>-G- | --- | --- | --- | --- | --- | --- | --- | --- | --- | --- | --- |
| G30.4 |  | --- | --- | --- | --- | --- | --- | --- | --- | --- | --- | --- | --- | --- | S<br>--C | R<br>-G- | --- | --- | --- |
| G30.5 |  | --- | --- | --- | --- | --- | --- | --- | --- | --- | --- | --- | --- | --- | S<br>--C | --- | --- | --- | --- |
| G30.6 |  | --- | --- | --- | --- | --- | --- | --- | --- | --- | --- | --- | --- | --- | --- | --- | --- | --- | --- |
| G30.7 |  | --- | --- | --- | --- | --- | --- | --- | --- | --- | --- | --- | --- | --- | S<br>--C | --- | --- | --- | --- |
| G30.8 |  | --- | --- | --- | --- | --- | --- | --- | --- | --- | --- | --- | --- | --- | --- | --- | --- | --C | --- |
| G30.9 |  | --- | --- | --- | --- | --- | --- | --- | --- | --- | --- | --- | --- | R<br>-G- | --- | --- | --- | --- | --- |
| G30.10 |  | --- | --- | --- | --- | --- | --- | --- | --- | --- | --- | --- | --- | --- | S<br>--C | --- | --- | --- | --- |

Fig. 11B2

|  | A | S | G | F | T | V | +30 S | S | N | Y | M | S | W | V | R | Q | A | +40 P | G | K |
|---|---|---|---|---|---|---|---|---|---|---|---|---|---|---|---|---|---|---|---|---|
|  |  |  |  |  |  |  |  |  | CDR1 |  |  |  |  |  |  |  |  |  |  |  |
|  | GCC | TCT | GGG | TTC | ACC | GTC | AGT | AGC | AAC | TAT | ATG | AGC | TGG | GTC | CGC | CAG | GCT | CCA | GGG | AAG |
|  |  |  |  |  |  |  |  |  |  | E | | | G | | | | | | | |
|  |  |  |  |  |  |  |  |  |  | G-G | | | G-- | | | | | | | |
|  | --- | --- | --- | --- | --- | --- | --- | --- | --- | --- | --- | --- | --- | --- | --- | --- | --- | --- | --- | --- |
|  | --- | --- | --- | --- | --- | --- | --- | --- | --- | --- | --- | --- | --- | --- | --- | --- | --- | --- | --- | --- |
|  | --- | --- | --- | --- | --- | --- | --- | --- | --- | --- | --- | --- | --- | --- | --- | --- | --- | --- | --- | --- |
|  | --- | --- | --- | --- | --- | --- | --- | --- | --- | --- | --- | --- | --- | --- | --- | --- | --- | --- | --- | --- |
|  | --- | --- | --- | --- | --- | --- | --- | --- | --- | --- | --- | --- | --- | --- | --- | --- | --- | --- | --- | --- |
|  | --- | A G- | --- | --- | --- | --- | --- | --- | T C- | --- | --- | --- | --- | --- | --- | --- | --- | --- | --- | --- |
|  | --- | --- | --- | --- | --- | --- | --- | --- | H C- | --- | R G- | R C- | --- | --- | --- | --- | --- | --- | --- | --- |
|  | --- | A G- | --- | --- | --- | --- | --- | --- | --- | --- | --- | --- | --- | --- | --- | --- | --- | --- | T -C | --- |
|  | --- | --- | --- | --- | --- | --- | --- | --- | --- | --- | --- | --- | --- | --- | --- | --- | --- | --- | --- | --- |
|  | --- | --- | --- | --- | --- | --- | --- | --- | H C- | S -C | --- | --- | --- | --- | --- | --- | --- | --- | --- | --- |
|  | --- | -G | --- | --- | --- | --- | --- | --- | --- | --- | --- | --- | --- | --- | --- | --- | --- | --- | --- | --- |
|  | --- | --- | --- | --- | --- | --- | --- | --- | --- | --- | --- | --- | --- | --- | --- | --- | --- | --- | --- | --- |

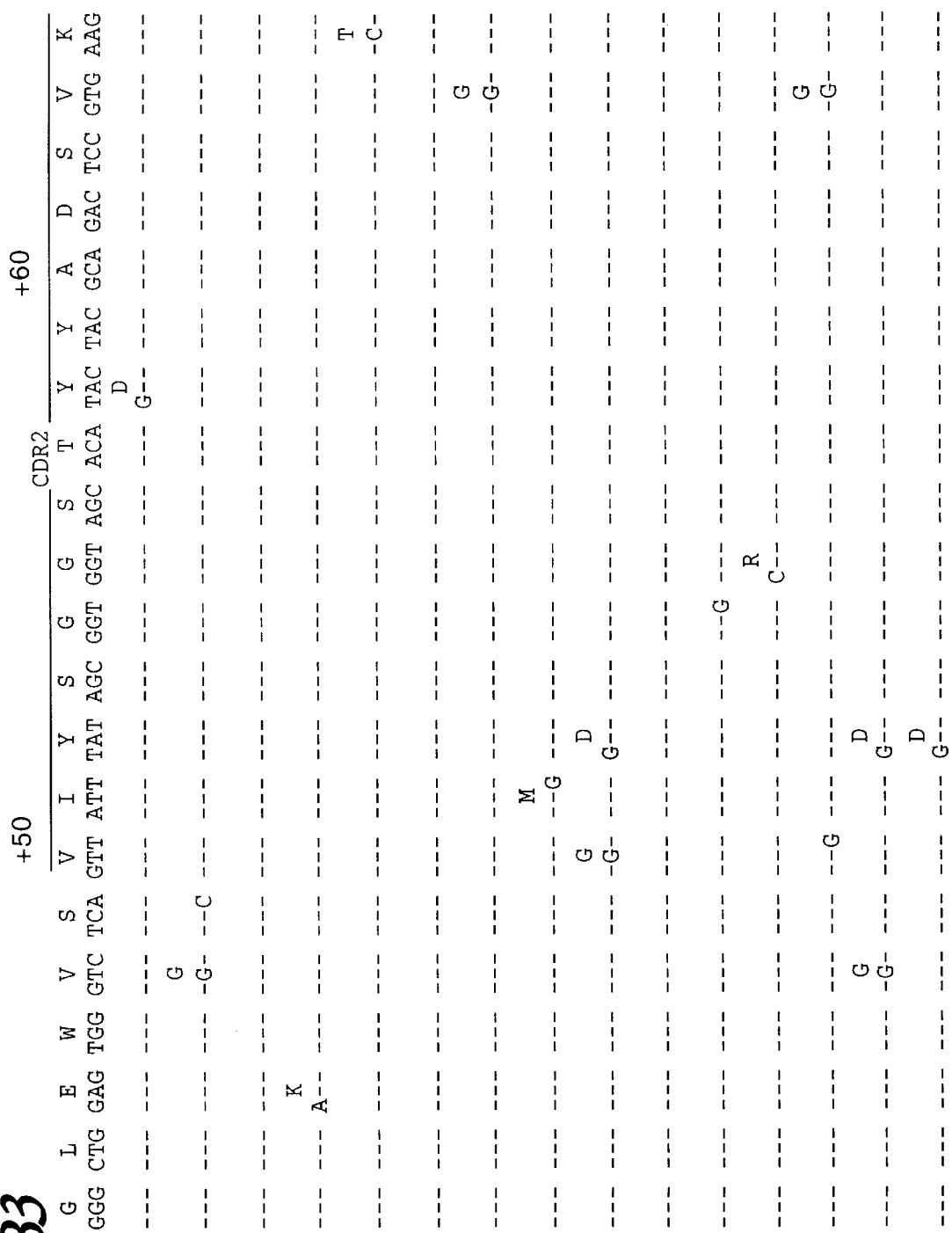
Fig. 11B3

Fig. 11B4

|   |   |   |   | +70 |   |   |   |   |   |   |   | +80 |   | +82 | a | b | c |
|---|---|---|---|---|---|---|---|---|---|---|---|---|---|---|---|---|---|
| G | R | F | T | I | S | R | D | N | S | K | N | T | L | Y | L | Q | M | N | S | L |
| GGC | CGA | TTC | ACC | ATC | TCC | AGA | GAC | AAT | TCC | AAG | AAC | ACG | CTG | TAT | CTG | CAA | ATG | AAC | AGC | CTG |
| --- | --- | --- | --- | --- | --- | --- | --- | --- | --- | --- | --- | --- | --- | --- | --- | --- | --- | --- | --- | --- |
| --- | --- | --- | --- | --- | --- | --- | --- | --- | --- | --- | --- | --- | --- | --- | --- | --- | --- | H C-- | --- | --- |
| --- | --- | --- | --- | --- | --- | C-- | --- | --- | --- | --- | --- | --- | --- | --- | --- | --- | --- | --- | --- | --- |
| --- | --- | C -G- | --- | S -G- | --- | --- | --- | --- | A G-- | --- | --- | --- | --- | S -C- | --- | --- | --- | --- | --- | --- |
| --- | --- | --- | --- | L -C- | --- | --- | --- | --- | --- | --- | S -G- | --- | R -G- | --- | --- | --- | --- | --- | R C-- | --- |
| --- | --- | --- | --- | --- | --- | --- | --- | --- | --- | --- | --- | --- | --- | --- | --- | --- | --- | --- | --- | --- |
| --- | --- | --- | --- | --- | --- | --- | --- | --- | --- | --- | --- | --- | --- | --- | --- | H -C | --- | --- | --- | --- |
| --- | --- | --- | --- | --- | --- | --- | --- | --- | --- | --- | H C-- | --- | --- | S -C- | --- | --- | --- | --- | --- | --- |
| --- | --- | V G-- | --- | --- | --- | --- | --- | --- | --- | --- | --- | --- | --- | --- | --- | --- | R -G- | --- | --- | --- |

Fig. 11B5

| +83 | R | A | E | D | T | A | V | Y | Y | C | A | R |
|---|---|---|---|---|---|---|---|---|---|---|---|---|
| | R | A | E | D | T | A | V | Y<br>S | Y | C | A | R |
| | AGA | GCT | GAG | GAC | ACG | GCC | GTG | TAT | TAC | TGT | GCA | AGA |
| | --- | --- | --- | --- | --- | --- | --- | -C- | --- | --- | --- | --- |
| | --- | --- | --- | --- | --- | --- | --- | --- | --- | --- | --- | --- |
| | --- | --- | --- | --- | --- | --- | --- | --- | --- | --- | --- | --- |
| | --- | --- | --- | --- | --- | --- | --- | --- | --- | --- | --- | C-- |
| | --- | -G- | --- | --- | --- | --- | --- | --- | --- | --- | --- | --- |
| | --- | --- | --- | --- | --- | --- | --- | --- | D<br>G-- | --- | --C | --- |
| | --- | --- | --- | --- | --- | --- | --- | --- | --- | --- | --- | --- |
| | --- | --- | --- | --- | --- | --- | --- | --- | --- | --- | --C | --- |
| | --- | --- | --- | --- | --- | --- | --- | --- | --- | --- | --C | --- |
| | --- | --- | --- | --- | --- | --- | G-- | --- | --- | --- | --- | --- |
| | --- | --- | --- | --- | --- | --- | -G- | --- | --- | --- | --- | --- |
| | --- | --- | --- | --- | --- | --- | G-- | --- | --- | --- | --- | --- |
| | --- | --- | --- | --- | --- | --- | G-- | --- | --- | --- | --- | --- |
| | --- | --- | --- | --- | --- | --- | --- | --- | --- | G-- | --- | --- |
| | --- | --- | --- | --- | --- | --- | --- | --- | --- | G-- | --- | --- |
| | --- | --- | --- | --- | --- | --- | --- | --- | --- | --- | --- | --- |
| | --- | --- | --- | --- | --- | --- | --- | --- | --- | --- | --- | C-- |

Fig. 11C1

|  | E | S | G | G | G | L | I | Q | P | G | G | S | L | R | L | S | C | A | A |
|---|---|---|---|---|---|---|---|---|---|---|---|---|---|---|---|---|---|---|---|
|  | GAG | TCT | GGA | GGA | GGC | TTG | ATC | CAG | CCT | GGG | GGG | TCC | CTG | AGA | CTC | TCC | TGT | GCA | GCC |
| 22 |  |  |  |  |  |  |  |  |  | -A |  |  |  |  |  |  |  |  |  |
| P+G8.2 |  |  |  |  |  |  |  |  |  |  |  |  |  |  |  |  |  |  |  |
| P+G8.3 |  |  |  |  |  |  |  |  |  |  |  |  |  |  |  |  | R |  |  |
|  |  |  |  |  |  |  |  |  |  |  |  |  |  |  |  |  | C-- |  |  |
| P+G8.4 |  |  |  |  |  | S |  |  |  |  |  |  |  |  |  |  |  |  |  |
|  |  |  |  |  |  | -C- |  |  |  |  |  |  |  |  |  |  |  |  |  |
| P+G8.5 |  |  |  |  |  |  |  |  |  |  |  |  |  | -G |  |  |  |  |  |
| P+G12.1 |  |  |  |  |  |  |  |  |  |  |  |  |  |  | -T |  |  |  |  |
| P+G12.2 |  |  |  |  |  |  | V | R |  |  |  |  |  |  |  |  |  |  |  |
|  |  |  |  |  |  | C-- | G-- | -G |  |  |  |  |  |  |  |  |  |  |  |
| P+G30.1 |  |  |  |  |  |  |  |  |  |  | F |  |  | -G | P | P |  | T | V |
|  |  |  |  |  |  |  |  |  |  |  | -T- |  |  |  | -C- | C-- |  | A- | -T- |
| P+G30.2 |  |  |  |  |  |  | V |  |  | E | E P |  |  | G |  |  |  |  |  |
|  |  |  |  |  |  |  | G-- |  |  | -A | -A- C- |  |  | G-G |  |  |  |  |  |
| P+G30.4 |  |  |  |  |  |  |  |  |  |  | -A |  | -A | -G |  |  |  |  |  |
| P+G30.5 |  |  |  |  |  | V |  |  |  |  |  |  |  | G |  |  |  |  |  |
|  |  |  |  |  |  | G-- |  |  |  |  |  |  |  | G-- |  |  |  |  |  |
| P+G30.7 | G |  |  |  |  |  |  | R |  |  | P |  |  | G |  |  | C |  | G |
|  | -G- |  |  |  |  |  |  | -G |  |  | C- |  |  | G-- |  |  | -C |  | -G |
| P+G30.8 |  |  |  |  |  |  |  |  |  |  | P |  |  | G | P |  | R | V | T |
|  |  |  |  |  |  |  |  |  |  |  | C-- |  |  | G-G | -C- |  | R-- | -T- | -T- |
| P+G30.9 |  |  |  |  |  |  |  |  |  |  | P |  |  | G | P |  | C |  | T |
|  |  |  |  |  |  |  |  |  |  |  | C-- |  |  | G | -CT |  | -C |  | A-- |
| P+G30.10 |  |  |  |  |  | C-- |  |  |  |  |  | -T |  | G-G | F | C-- | R |  |  |
|  |  |  |  |  |  |  |  |  |  |  |  |  |  |  | -T- |  |  |  |  |

+10 +20

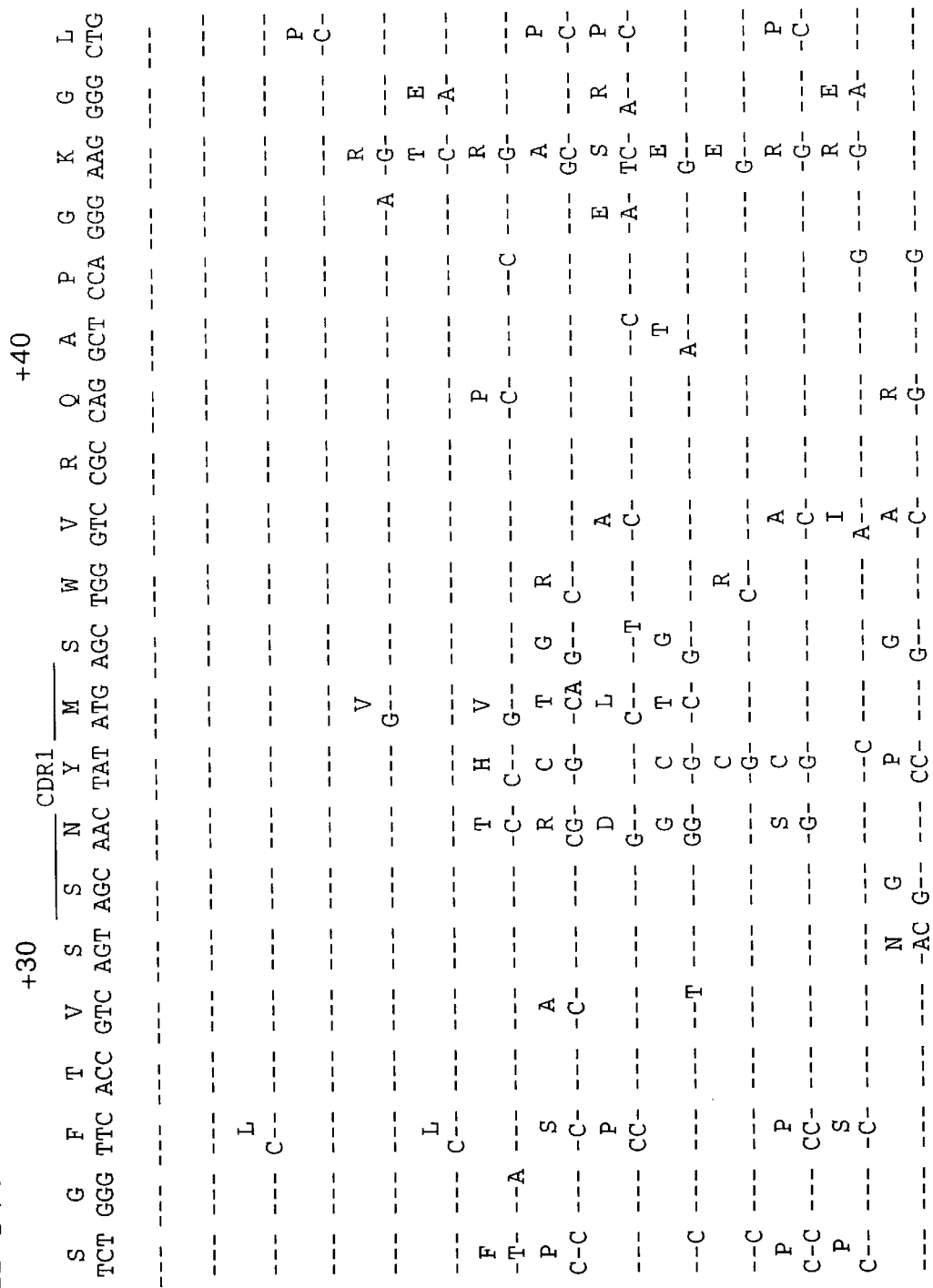
Fig. 11C2

Fig. 11C3

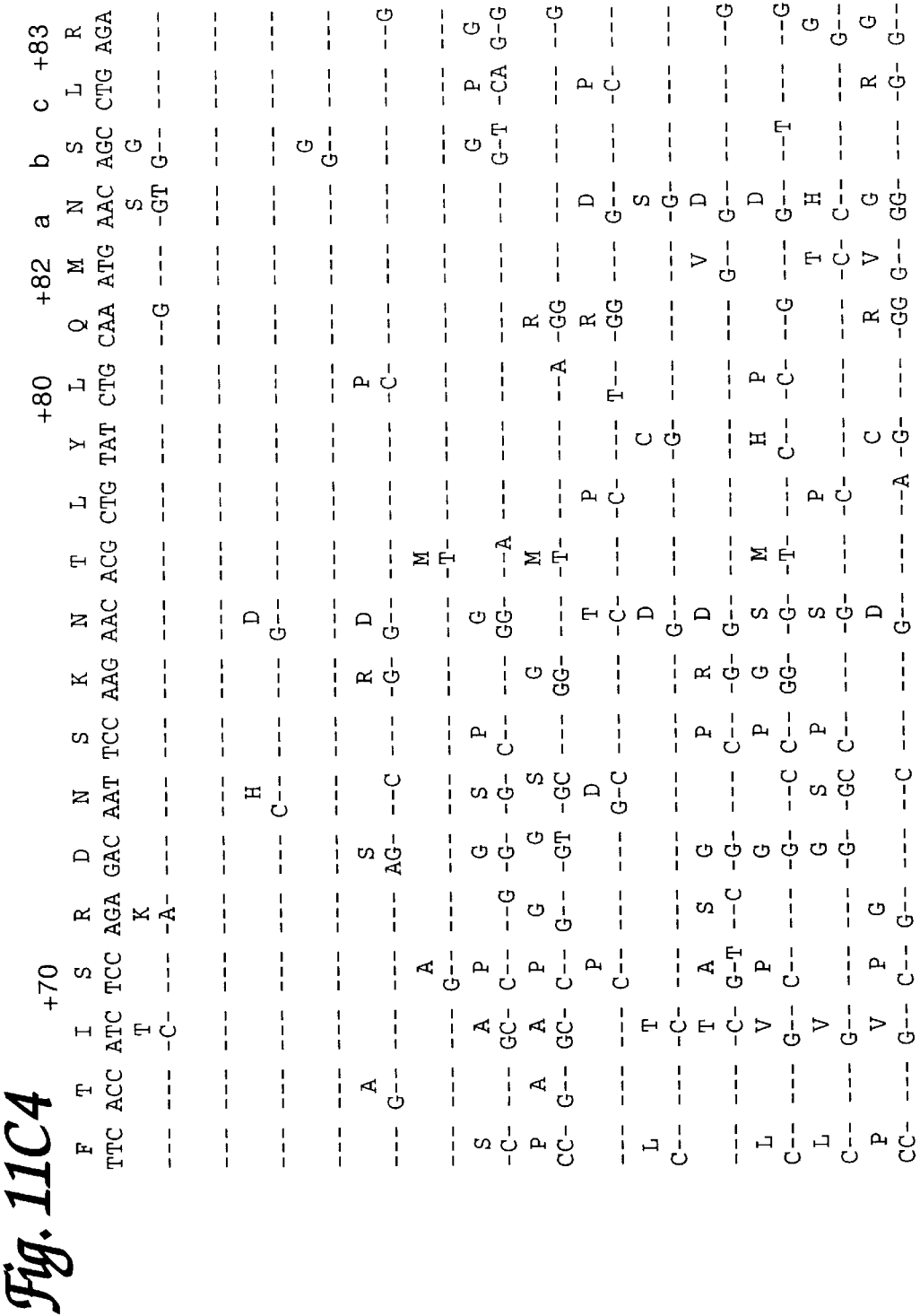
Fig. 11C4

Fig. 11C5

RELATING TO MUTAGENESIS OF NUCLEIC ACIDS

FIELD OF THE INVENTION

This invention relates to certain novel compounds, a method of mutating a nucleic acid sequence involving the novel compound, and to a kit for performing the method of the invention.

BACKGROUND OF THE INVENTION

In vitro site-directed mutagenesis, which involves the substitution of single amino acids in a protein by changing the relevant base residues in the encoding DNA, has proved to be a powerful method in protein engineering. This technique typically requires information on the structure-function relationship of the protein under study in order to provide a rationale for generating mutants with altered properties. In contrast, random mutagenesis of the DNA region of interest coupled with adequate screening or selection procedures provides an alternative and general method for the generation of DNA, RNA or protein species with improved or novel functions in the absence of initial structural information.

Several methods for the generation of mutants of large DNA fragments have been described and involve using pools of random sequence synthetic oligonucleotides (Matteucci & Heyneker, Nucl. Acids Res. 1983 11, 3113; Wells et al., Gene 1985 34, 315; Nerr et al., DNA 1988 7, 127 and references therein), chemical modification of the target sequence (Kadonaga & Knowles, Nucl. Acids Res. 1985 13, 1733; Meyers et al, Science 1985 229, 242, and references described therein); or base misincorporation using an error-prone polymerase (Lehtovaara et al, Protein Eng. 1988 2, 63).

The synthetic oligonucleotide approach is restricted by the length of the DNA amenable to chemical synthesis, whilst the chemical approach is often labour intensive. In other approaches, random mutations are generated using the polymerase chain reaction (PCR). One such method relies exclusively on the intrinsic error frequency of Taq DNA polymerase, resulting in about $0.5 \times 10^{-3}$ mutations per base pair (Zhou, Nucl. Acids Res. 1991 19, 6052). In an improved variation of this method the target sequence of interest is copied under conditions which further reduce the fidelity of DNA synthesis catalysed by Taq DNA polymerase e.g. by the addition of the cofactor manganese and by the use of high concentrations of magnesium and the relevant deoxy-nucleoside triphosphates (dNTPs—see Leung et al., Techniques 1989 1, 11). Using the latter procedure mutation frequencies in the order of $20 \times 10^{-3}$ mutations per base pair have been claimed.

An alternative approach to PCR-based random mutagenesis is to replace, partially or fully, the 5'-triphosphates of the four natural nucleosides by the triphosphates of nucleoside analogues which display ambivalent base pairing potential. To our knowledge this approach has only been attempted using deoxyinosine triphosphate—dITP (Spee et al, Nucl. Acids Res. 1993 21, 777; Ikeda et al, J. Biol. Chem. 1992 267, 6291). However, this analogue is a poor substrate for Taq Polymerase and cannot support DNA synthesis when replacing any of the four normal dNTPs. As a result, four separate PCR reactions are required containing dITP and three dNTPs in equal concentrations together with limiting concentrations of the fourth dNTP. The four separate PCR products are then pooled and cloned (Spee et al., cited above).

A general feature of the above procedures is that the yield of mutant sequences is low and that the pattern of mutations is heavily biased towards transitions (pyrimidine-pyrimidine or purine-purine substitutions). In addition, with the last two methods, undesirable base additions or deletions occur at an appreciable rate.

In an alternative approach, it was envisaged that the 5'-triphosphates of a pyrinidine or purine nucleoside analogue capable of inducing transition mutations in combination with other triphosphate analogues capable of causing transversion mutations would allow efficient random mutagenesis via PCR. The nucleoside analogues P (Kong Thoo Lin & Brown, Nucl. Acids Res. 1989 17, 10373) and K (Brown & Kong Thoo Lin, Carbohydrate Res. 1991 216, 129), (structures 1 and 3 respectively, shown in FIG. 1) have previously been incorporated into oligonucleotides and demonstrate ambivalent base pairing potential, as illustrated for P in FIG. 2. That is, P forms base pairs of equivalent stability with adenine and guanine. Likewise K forms base pairs with closely similar stabilities with thymine and cytosine. In addition, template DNA containing these analogues is recognised by polymerases such as Taq polymerase in PCR and Sequenase™ in DNA sequencing (Kong Thoo Lin & Brown, Nucleic Acids Res. 1992 20, 5149; Kamiya et al., Nucleosides & Nucleotides 1994 13, 1384; Brown & Kong Thoo Lin, Collect. Czech. Chem. Commun. (Special issue), 1990 55, 213). The present inventors considered that other analogues, e.g. 2'-deoxy-8-hydroxyguanosine 5'-triphosphate, abbreviated as 8oxodGTP (Pavlov et al, Biochemistry 1994 33, 4695), shown as structure 5 in FIG. 1, might be valuable in this context in order to generate transversion mutations.

SUMMARY OF THE INVENTION

In a first aspect the invention provides a compound having the structure set forth below:-

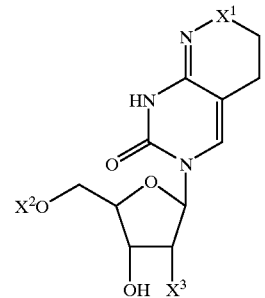

where $X^1$=O, S, N-alkyl; $N^+$-dialkyl, or N-benzyl $X^2$=triphosphate $(P_3O_9)^{4-}$, diphosphate $(P_2O_6)^{3-}$, thiotriphosphate $(P_3O_8S)^{4-}$, or analogues thereof, but not H; and $X^3$=H, $NH_2$, F or OR, where R may be any group, but is preferably H, methyl, allyl or alkaryl.

These compounds have not previously been synthesised. In preferred embodiments $X^2$ is triphosphate. Conveniently, $X^1$ is O, and preferably $X^3$ is H or OH. Typically R is H, methyl, allyl or alkaryl. A compound "dP" which has been synthesised previously (and which is outside the scope of the claims) has the general structure above where $X^1$ is O, $X^2$ is H (such that the compound is not within the scope of the invention), and $X^3$ is OH. A novel compound within the scope of the invention, and which represents a preferred embodiment thereof, is the triphosphate of dP, termed dPTP.

The compounds of the present invention, and dPTP in particular, have unexpected properties (some of which are described below) which could not have been predicted from the prior art, rendering the invention non-obvious. The compounds of the invention may act as nucleoside triphosphate analogues (especially where $X^3$ is H or OH) and thus have a wide range of potential uses, one of which is described in detail below.

The present invention also relates to the synthesis of hydrogen bond ambivalent purine and pyrimidine nucleoside triphosphates and their application in PCR-based random mutagenesis, and to the generation of polynucleotide libraries (particularly, large libraries) based on an original defined template sequence from which the single species are obtained by simple cloning methods. In particular the invention involves the synthesis and use of the novel degenerate pyrimidine deoxynucleoside triphosphates of the type shown in structure 6, (in FIG. 1) together, in preferred embodiments, with analogues of the types shown in structure 5 and/or structure 4 (in FIG. 1). The invention is exemplified using a PCR-based system for random mutagenesis of DNA sequences, which employs mixtures of the novel triphosphate dPTP (structure 2 in FIG. 1, synthesis of which is described in detail below), in conjunction with the already known analogue 8-oxodGTP (structure 5, where $R'=NH_2$), (Mo et al, Proc. Natl. Acad. Sci. USA. 1992 89, 11021).

In a second aspect therefore the invention provides a method of mutating a nucleic acid sequence, comprising replicating a template sequence in the presence of a nucleotide analogue according to the general structure defined above, so as to form non-identical copies of the template sequence comprising the nucleotide analogue residue. In a preferred embodiment the nucleotide analogue is 6-(2-deoxy-β-D-erythropentofuranosyl)-3,4-dihydro-8H-pyrimido-[4,5-c][1,2]oxazine-7-one 5'-triphosphate (abbreviated as deoxyP triphosphate or dPTP).

It will be apparent to those skilled in the art that slight modifications to the structure of dPTP may be effected without substantially disrupting the utility of the compound for use in the method of the invention. Accordingly, such slightly modified forms of dPTP may be regarded as functional equivalents of dPTP and their use is intended to fall within the scope of the invention defined above. Particular examples of such modified forms are shown in structure 6 in FIG. 1, where X may be S, N-alkyl (particularly N-methyl, N-ethyl or N-propyl), $N^+$-dialkyl (e.g. dimethyl, diethyl or dipropyl) or N-benzyl (with or without substitutions in the benzene ring). The group at position X, when the analogue is incorporated into DNA, is thought to project into the major groove of the double helix, such that quite bulky groups can be successfully accommodated. With the benefit of the disclosure contained herein, and in the publication of Loakes & Brown (1995 Nucleosides and Nucleotides 14, 291), the above modifications, and possibly others, will be apparent to those skilled in the art.

The "non-identical copies" produced by the method are DNA sequences synthesised from a template (and thus may be considered copies thereof) but contain one or more mutations relative to the template and so are not identical thereto. Typical mutation frequencies attained by the present invention are in the range 1 to 20%, more particularly 2 to 10%, but it will be appparent to those skilled in the art from the information contained herein that the mutation frequency can be controlled (which is an advantage of the present invention) to set the limit at the desired level. For most purposes however the range of 1 to 20% for mutation frequency will be preferred. This range is sufficiently high as to be reasonably likely to introduce a significant change in the transcription and/or translation product, but is not so high as to inevitably abolish whatever desirable characteristics may have been possessed by the transcription or translation products of the template sequence.

Preferably the template sequence is replicated by a method comprising the use of an enzyme, desirably a DNA polymerase without a 3,5'-exonuclease "editing" function, conveniently by performance of the Polymerase Chain Reaction (PCR). typically using a thermostable enzyme such as Taq polymerase. Conveniently, the template sequence will be replicated in the additional presence of the four normal dNTPs (i.e. dATP, dCTP, dGTP and TTP). Typically dPTP will be present in substantially equimolar ratio with the majority of the four normal dNTPs (although the relative concentrations may advantageously be altered, depending on the number and nature of mutations desired, and depending on the presence or absence of other reagents, as described below).

In preferred embodiments the template sequence will be replicated in the presence of one or more additional analogue triphosphates. Desirably such additional analogues will cause the introduction of transversion mutations. Suitable examples of desirable analogue triphosphates include dKTP and 8-oxodGTP (mentioned above) and $O^2$-ethylthymidine triphosphate (Singer et al., 1989 Biochemistry 28, 1478–1483)

Once the non-identical copies of the template sequence have been obtained, these are desirably replicated in the presence of the four normal dNTPs (namely dGTP, dCTP, dATP and TTP) but in the absence of analogues thereof, to replace the nucleotide analogue residues and "establish" the mutations. This second-stage replication may be performed in vivo (e.g. by introducing the non-identical copies, inserted into a vector or not, into a suitable laboratory organism, such as E. coli or other microorganism, which organism will then replace the dPTP residues in the introduced DNA by means of natural DNA repair machinery). Preferably however the second stage replication is performed in vitro, conveniently by means of PCR. This allows greater control over the number and type of mutations sought to be introduced into the DNA sequence and prevents the possibility that repair enzymes in the host (compared to performance of the second stage replication in vivo) might adversely affect the established mutations. It is found that the method of the present invention confers several advantages over the known prior art methods of mutagenesis.

Firstly, it yields a high frequency of sequences carrying point mutations which, for many investigative purposes, are the most informative types of mutations. Secondly the method produces insertion and deletion mutations only at an insignificant frequency. This is important because such mutations cause frame-shifts in coding sequences and so are generally undesirable. In addition, the desired transversion and transition mutations are obtained at a high rate, and all possible types of such transition mutations can be obtained. Use of PCR to replicate the template sequence is especially desirable as it allows control of the mutation frequency. The inventors have surprisingly found that there is a substantially linear correlation between the mutation frequency and the number of PCR cycles performed. This linear relation holds for up to about 30 PCR cycles and may extend over a wider range. In addition, further influence on mutation frequency may be effected by alteration of the concentration of deoxynucleoside triphosphates (and/or analogues thereof).

In summary therefore, the method of the invention differs from those previously described in a number of points, including: (i) it yields a high frequency of sequences carrying point mutations; (ii) it does not produce insertions and deletions at a significant frequency; (iii) it produces relatively high rates of transversion and transition mutations; (iv) all possible types of transition mutations, and some types of transversion mutations, can be generated; (v) it enables efficient mutagenesis to be conducted in a single DNA amplification reaction and (vi) it allows control of the mutational load in the amplified polynucleotide products inter alia through cycle number, and deoxynucleoside triphosphate ratios; and vii) it is suitable for randomisation of very long sequences (up to several kilobases), which has been problematical using prior art methods. Thus the use of appropriate mixtures of triphosphate derivatives of nucleoside analogues in accordance with the present invention enables highly controlled random mutagenesis of DNA sequences resulting in nucleotide substitutions in any DNA and corresponding amino acid substitutions in the derived polypeptides, which cannot efficiently be achieved by existing methods.

The method of the invention has clear utility in protein engineering. In addition, there is increasing interest in structure/function relationships in RNA molecules (see, for example Bartel & Szostak 1993 Science 261, 1411–1418).

Thus the method will be particularly useful for the construction of libraries of DNA sequences directing synthesis of variant transcription (i.e. RNA) or translation (i.e. polypeptide) products. In view of the difficulties previously presented in connection with prior art methods, the present invention will be especially useful in the preparation of libraries of long (several kilobases or more) sequences, which are not amenable to generation by other random mutagenesis methods.

In a further aspect the invention provides a kit for introducing mutations into a nucleic acid sequence, comprising dPTP, means for replicating a template sequence in the presence thereof so as to incorporate the analogue into non-identical copies of the template sequence, and instructions for performing the method defined above. Conveniently the means for replicating the template sequence comprises means for performing the polymerase chain reaction (PCR). The kit may advantageously further comprise 8-oxodGTP and/or dKTP, and/or $O^2$-ethylthymidine triphosphate.

In another aspect the invention provides a compound having the structure set forth below:

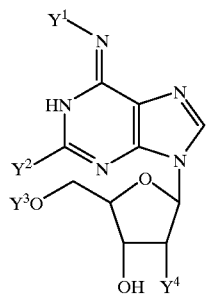

where $Y^1$=OH, O-alkyl, $NH_2$ or N(Alkyl)$_2$; $Y^2$=H, or $NH_2$; $Y^3$=triphosphate $(P_3O_9)^{4-}$ diphosphate $(P_2O_6)^{3-}$, thiotriphosphate $(P_3O_8S)^{4-}$, or analogues thereof, but not H; and $Y^4$=H, $NH_2$, F, or OR where R may be any group but is preferably H, methyl, allyl or alkaryl.

In preferred embodiments, $Y^1$ is $OCH_3$, $Y^3$ is triphosphate, and $Y^4$ is H or OH. A particular example of a preferred embodiment is the nucleotide analogue dKTP. The compounds of the invention have unexpected characteristics and a variety of potential applications, particularly as nucleotide analogues. The compounds may be used, for example, in a method of mutagenesis, similar to that described above in relation to the second aspect of the invention, the preferred features of which are generally common to both methods.

In yet a further aspect, the invention provides a method of making in vitro a DNA or RNA sequence comprising at least one base analogue, the method comprising treating in appropriate conditions a mixture comprising the four normal dNTPs (or rNTPs) and a novel nucleotide (or ribonucleotide) triphosphate analogue in accordance with the invention, with a DNA (or RNA) polymerase in the presence of template nucleic acid strand, so as to form a sequence of nucleotides (or ribonucleotides) comprising at least one analogue.

The invention will now be further described by way of example and with reference to the accompanying drawings, of which:

Figure 3A:
Figure 3B:
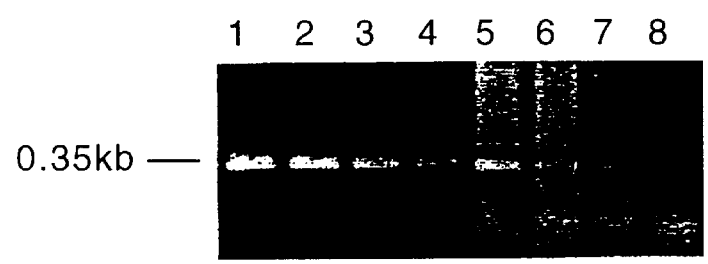

FIGS. 3A and 3B show photographs of gel electrophoresis of PCR products demonstrating incorporation into DNA and extension of dPTP (A) and 8-oxodGTP (B) by Taq polymerase—A) The PCR reaction mix included: dATP, dGTP, dCTP, TTP in sample 1; dGTP, dCTP, TTP, dPTP in sample 2; dATP, dGTP, TTP, dPTP in sample 3; dCTP, TTP, dPTP in sample 4; dATP, dGTP, TTP, dPTP in sample 5; dATP, dGTP, dCTP, dPTP in sample 6; dATP, dGTP, dPTP in sample 7; dATP, dGTP, dCTP, TTP, dPTP in sample 8. All dNTPs were at 500 µM, except in sample 4 and 7 where dPTP was at 1 mM.

Figure 3C:
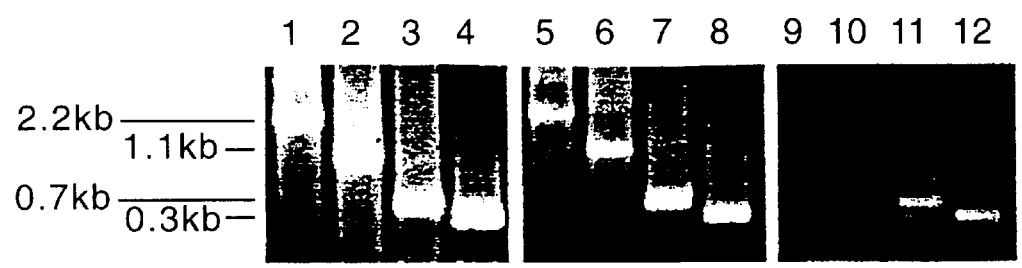
Figure 4C:
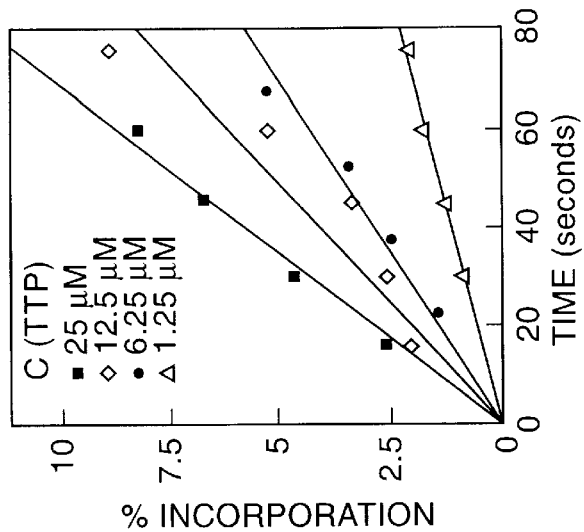
Figure 4B:
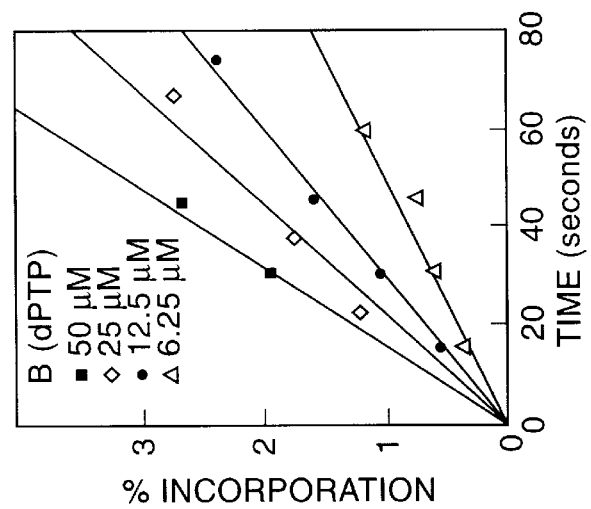
Figure 4A:
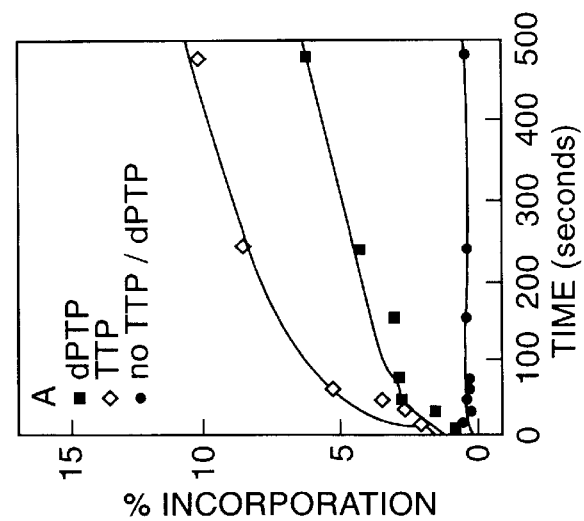

B) The PCR reaction mix included: dATP, dCTP and TTP at 500 µm. Samples 1 to 4 contained dGTP at 50 µM, 25 µM, 12.6 µM and 6.25 µM respectively, and 8-oxodGTP at 500 µM. Samples 5 to 8 contained the same decreasing amounts of dGTP but no 8-oxodGTP;

FIG. 3C shows a photograph of gel electrophoresis, demonstrating amplification by PCR of different target genes in the presence of the four natural dNTPs (lanes 1 to 4); equimolar concentrations of the four normal dNTPs and dPTP (lanes 5 to 8); and equimolar concentrations of the four normal dNTPs, dPTP and 8-oxodGTP (lanes 9 to 12). The template DNA was: human macrophage stimulating protein (MSP) (lanes 1, 5 and 9); human connexin 31 (lanes 2, 6 and 10); human connexin 43 (lanes 3, 7 and 11); or the ζ chain of human CD3 (lanes 4, 8 and 12). The size of the fragments is indicated at the side of the Figure in kilobases. All the fragments were cloned in pBluescript and DNA amplification was performed using standard T3 and T7 primers;

FIGS. 4A–C show: A time course of DNA synthesis in the presence of 12.5 µM [$^{32}$P]dCTP, dATP, dGTP and TTP (open diamonds) or dPTP (full squares). Primed M13mp18 was used as a template for DNA synthesis in the presence of 0.3 U Taq polymerase. FIGS. 4 B and C show the rate of DNA synthesis during the first 80 seconds of the reaction in the presence of 12.5 µM dATP, dGTP and [$^{32}$P]dCTP and the indicated concentrations of dPTP (B) and TTP (C);

FIGS. 5A–D show (Top): Plots of initial velocities against [dNTP] for the incorporation by Taq polymerase of dPTP opposite A (A), TTP opposite A (B), dPTP opposite G (C), and dCTP opposite G (D).

Figure 5A:
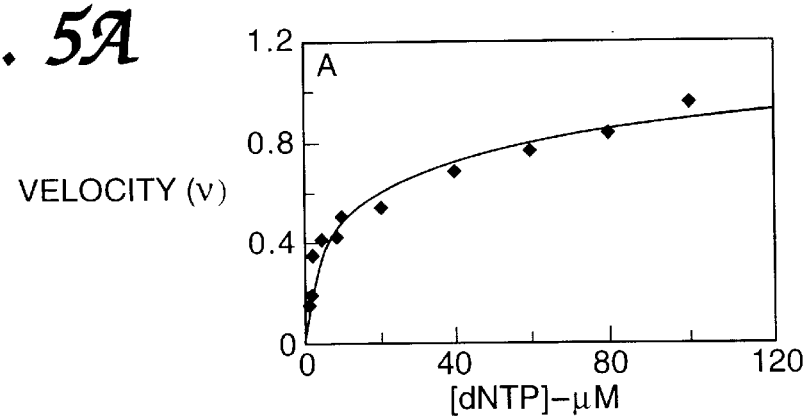
Figure 5B:
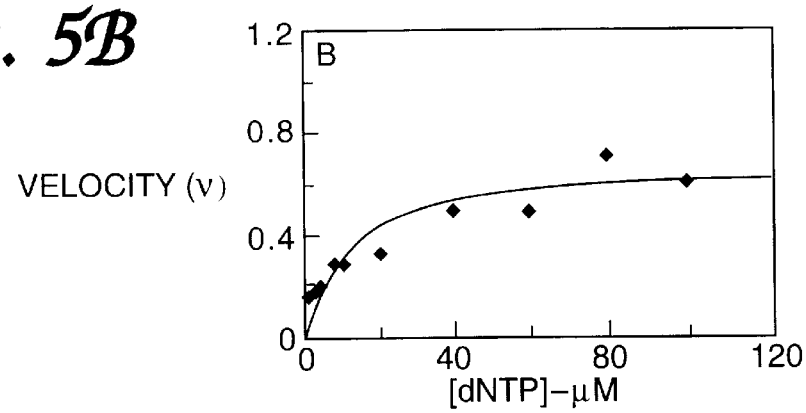
Figure 5C:
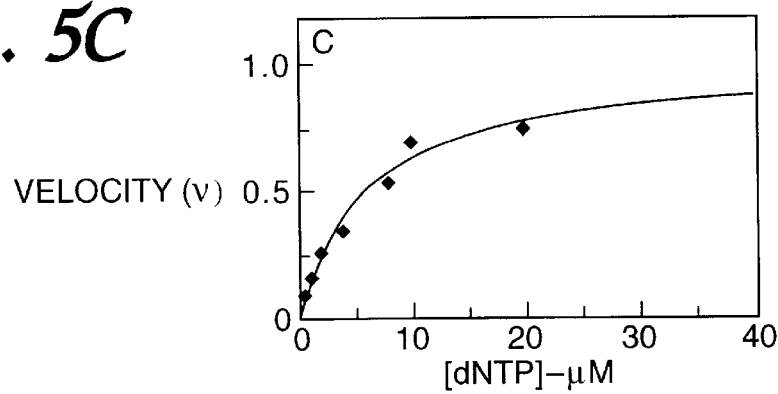
Figure 5D:
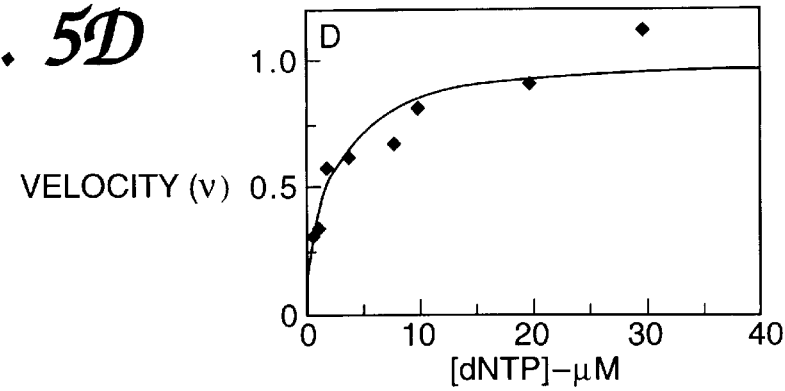
Figures 5E, 6:
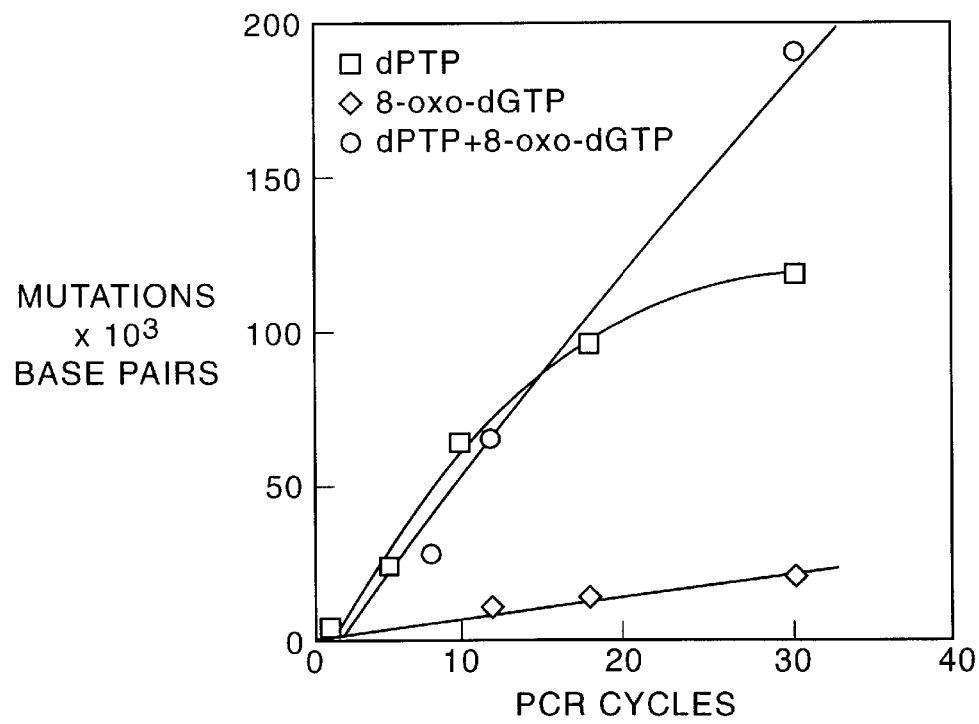
Figure 8A:
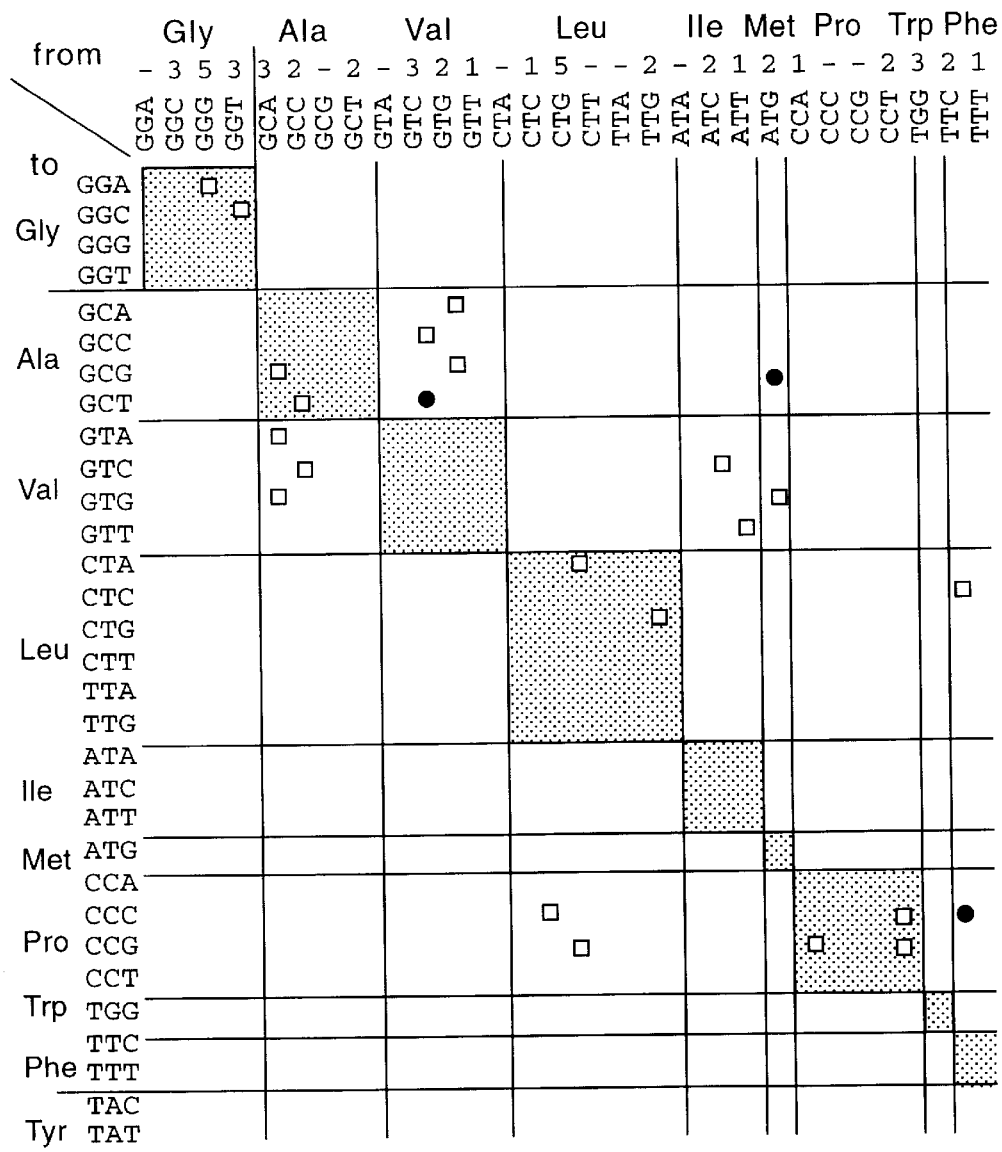
Figure 8B:
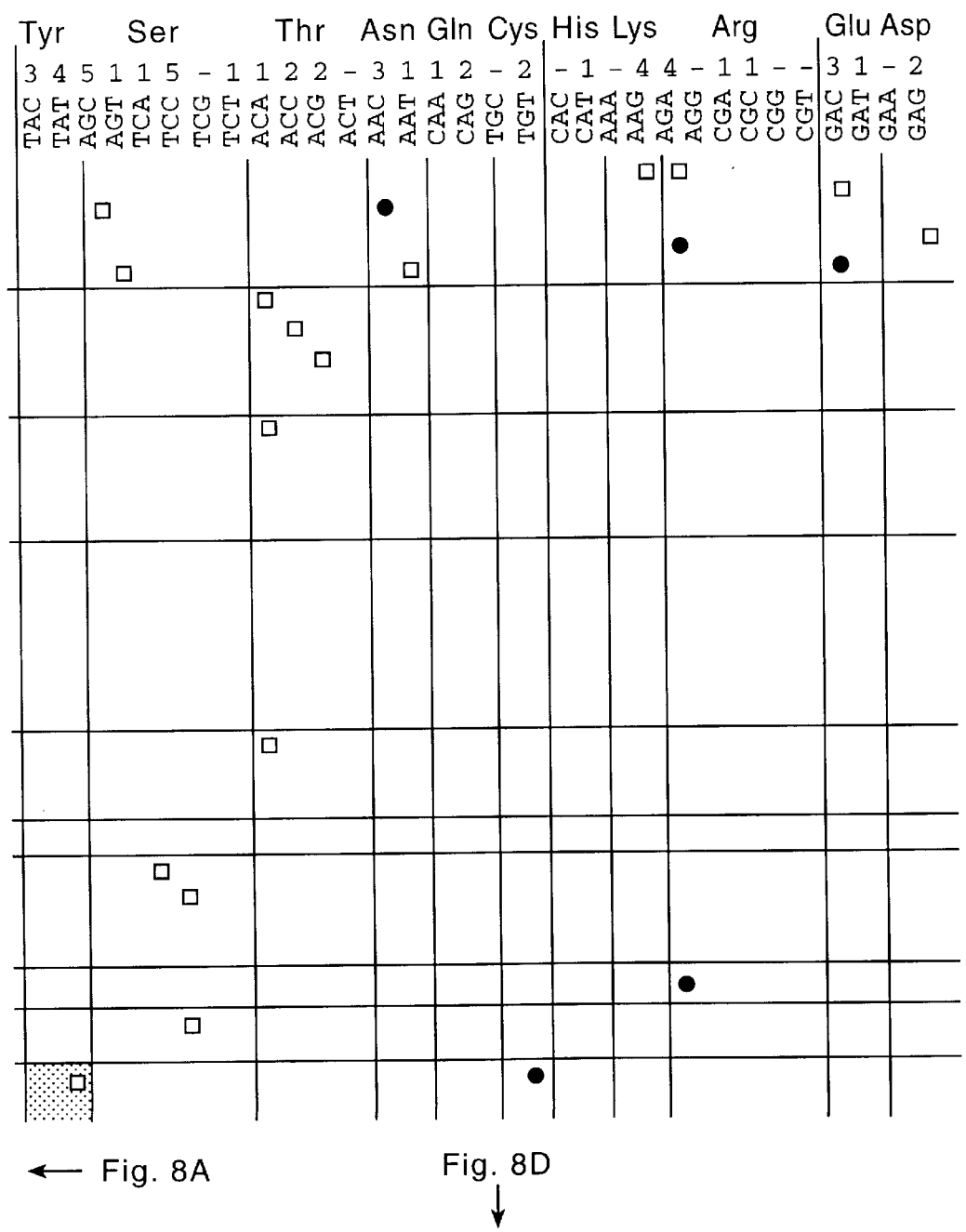
Figure 8C:
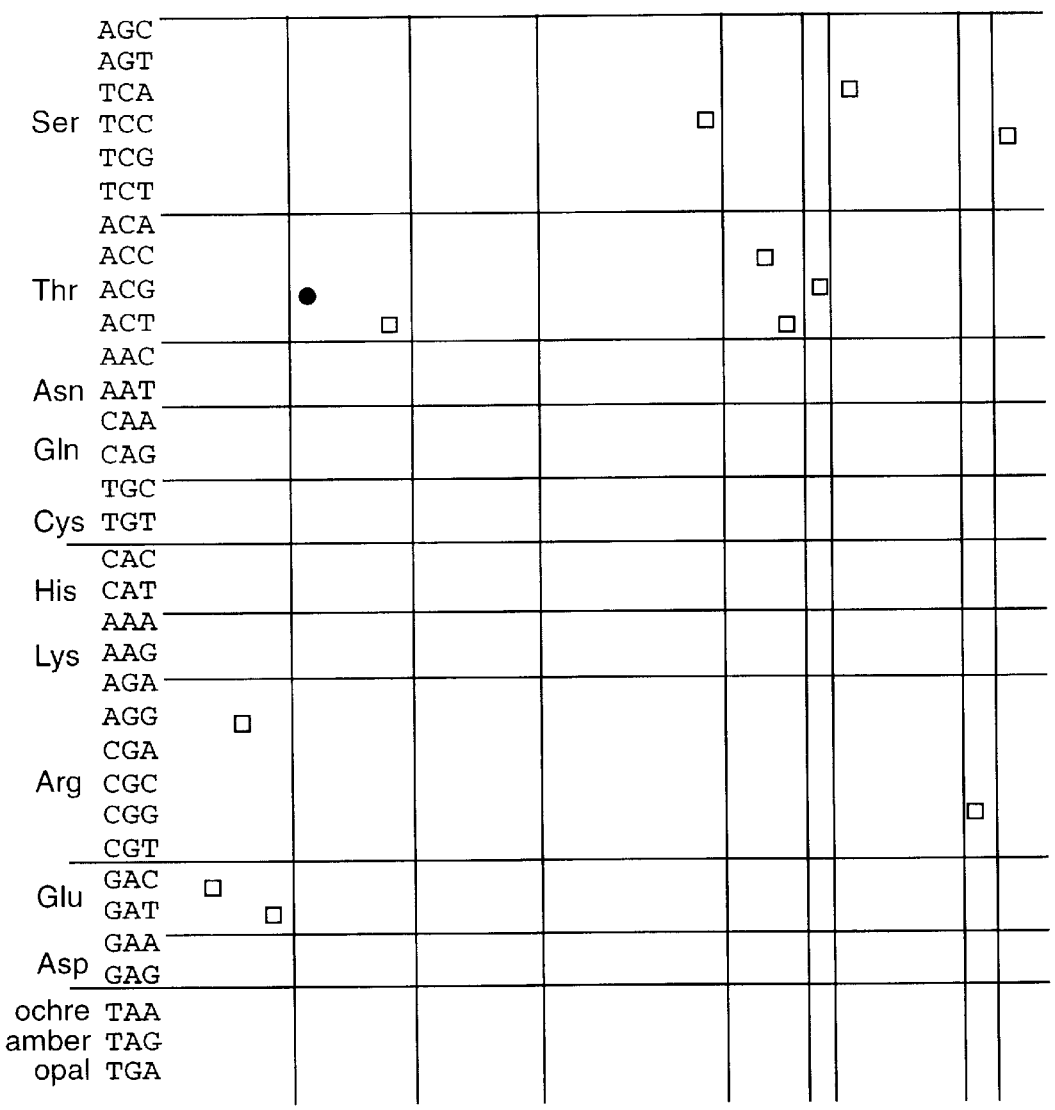
Figure 9A:
Figure 9D:
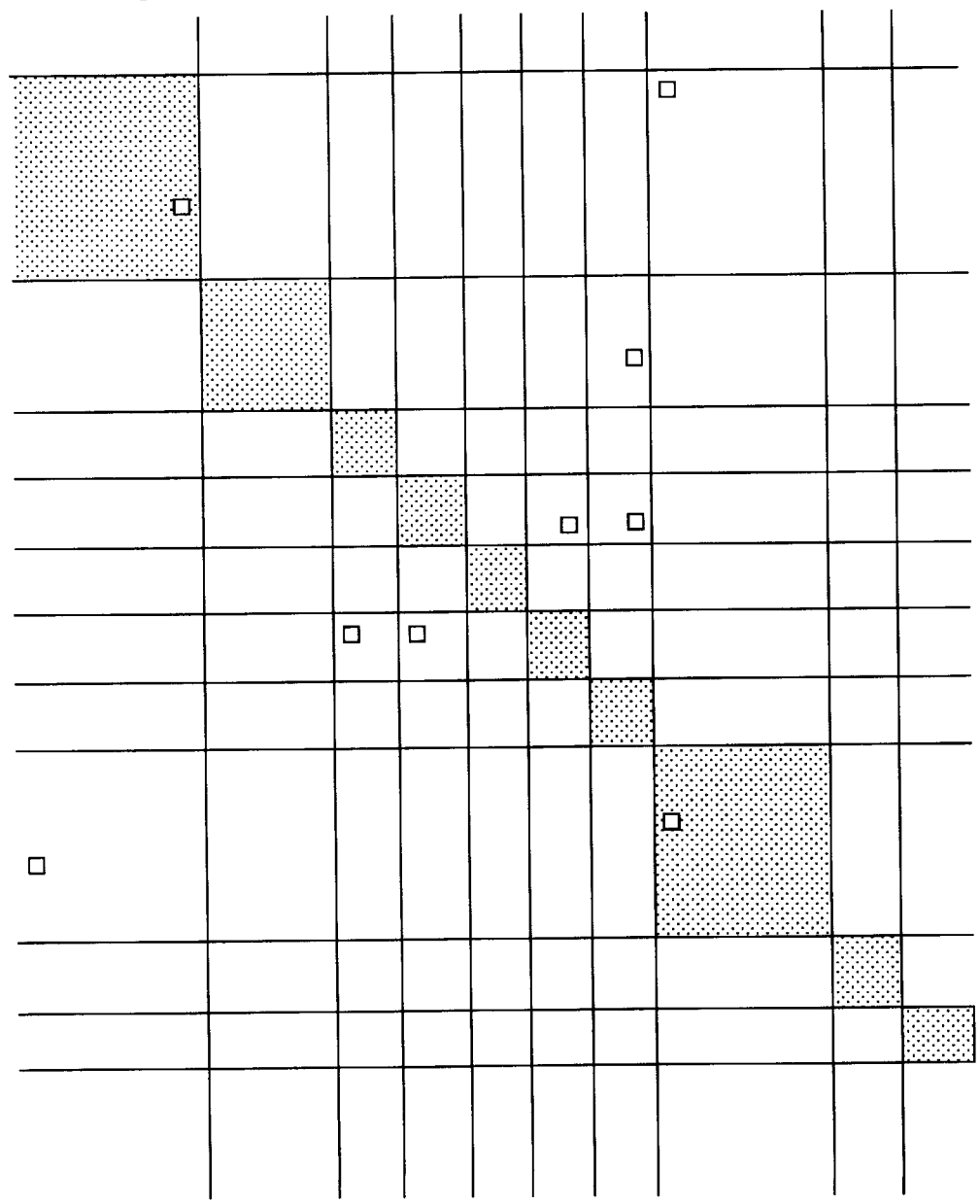
Figure 10B:
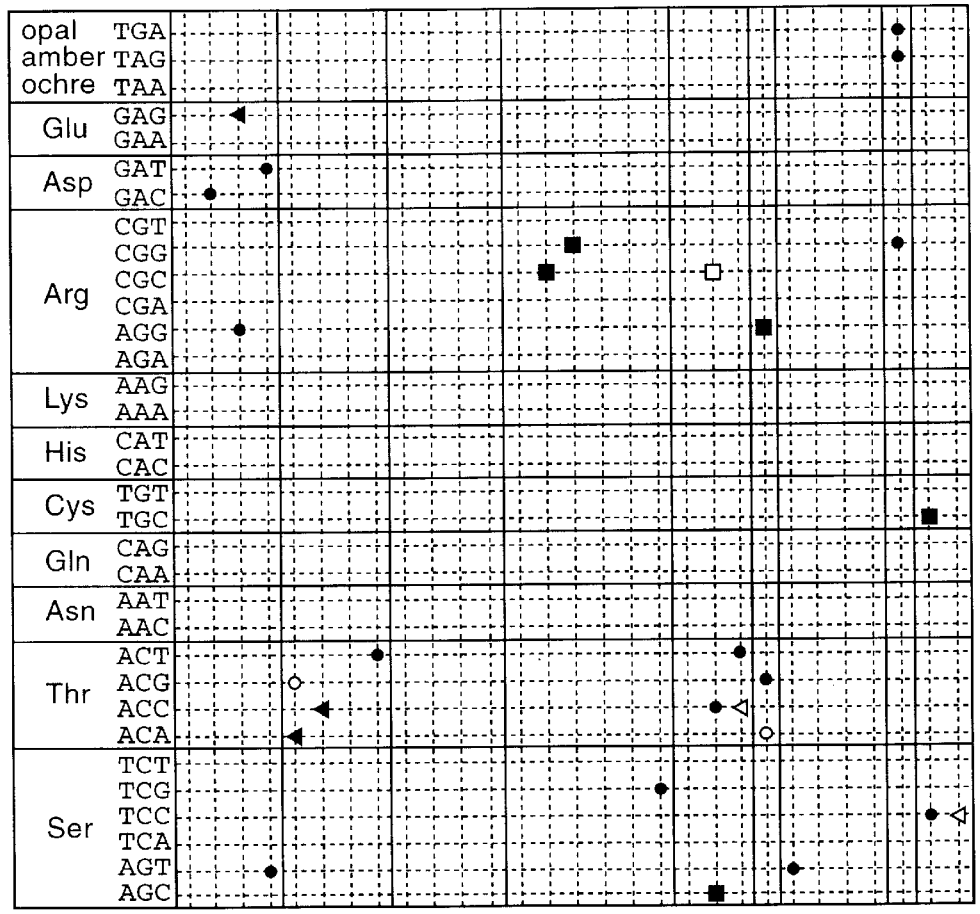
Figure 10D:
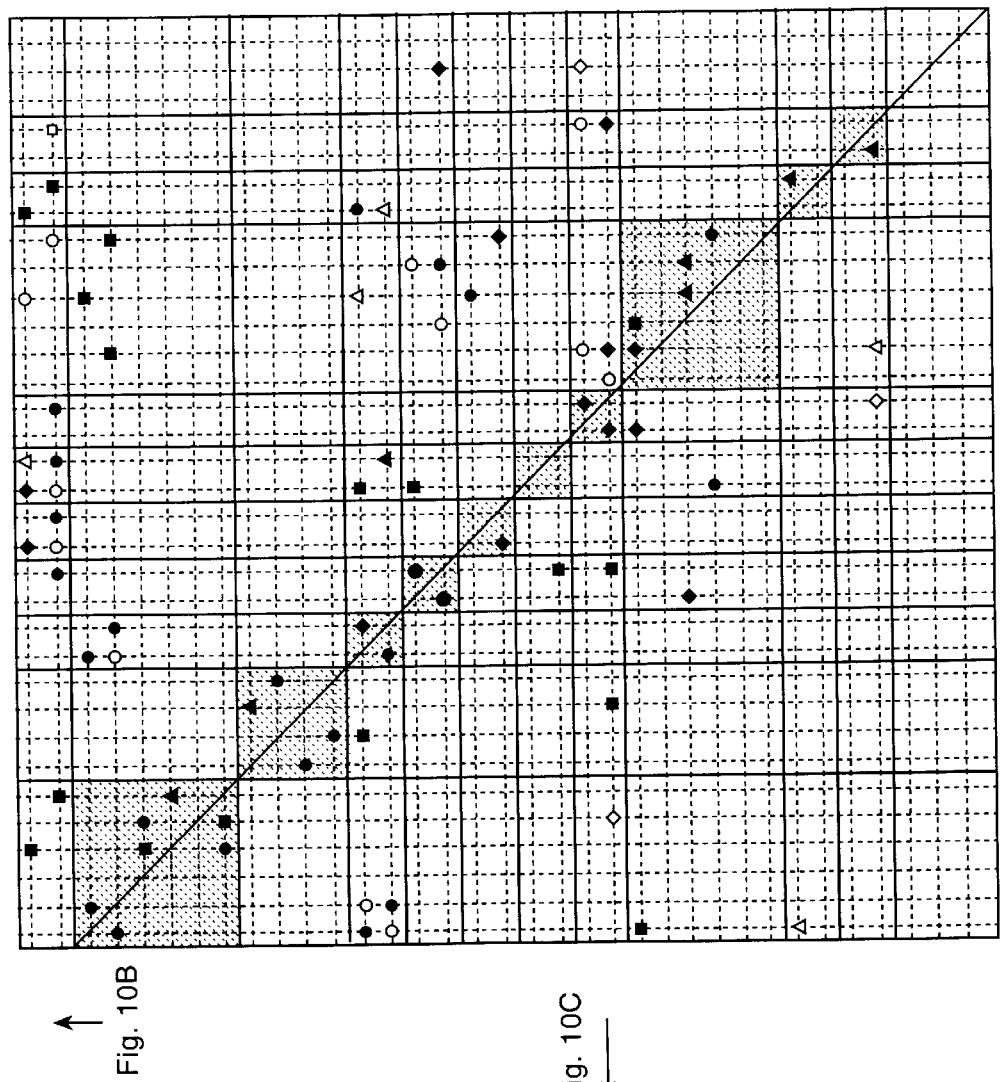

FIG. 5E shows primer and templates used in experiments (Seq ID No.s 3–5);

FIG. 6 shows the frequency of mutation of target DNA after different cycles of mutagenesis by PCR. The four normal dNTPs and the analogues were used in equimolar amounts (500 μM);

FIGS. 7A–7C show the pattern of mutations produced by dPTP, 8-oxodGTP and the mixture of the two. Data obtained after different number of PCR cycles have been pooled and figures express percentage of total number of mutations;

FIGS. 8A–8D show a summary of all the point mutations and the relative amino acid replacements produced by dPTP in the target DNA sequence MH22 (Griffiths et al., 1994 EMBO J. 13, 3245–3260) as shown by sequence analysis of 12 individual clones. Numbers at the top of the Table indicate how many times a particular codon is present in the target sequence. Open squares indicate single point mutations within a particular codon. Filled circles indicate two point mutations within a particular codon. In no case were three base substitutions found within a codon. Squares in shaded areas indicate silent mutations;

FIGS. 9A–9D comprise a summary of all the point mutations and the relative amino acid replacements produced by 8-oxodGTP in the target DNA sequence MH22 as shown by sequence analysis of 8 independent clones (legend as for FIGS. 8A–8D). The point mutation indicated with * (C→A) is not normally expected to result from mispairing of 8-oxodGTP;

FIGS. 10A–D show the codon changes produced by dPTP (circles), 8-oxodGTP (squares) and the combination of the two (triangles). Filled in symbols indicate a single nucleotide change within a codon, open symbols denote two nucleotide changes within the same codon. Diamonds indicate the presence of nucleotide changes different to those expected. Amino acids are grouped in five classes according to their physico-chemical characteristics: glycine, non-polar, polar, positively charged, and negatively charged. Asterisks denote codons which were not present in the two target genes studied; and FIGS. 11A1–4, 11B1-5, 11C1-5 shows mutations in the target DNA sequence MH22 (within dotted line, Seq ID No. 1, amino acid sequence is Seq ID No. 2) and corresponding amino acid substitutions (above dotted line) produced by dPTP (A), 8-oxodGTP (B) and the mixture of the two (C) when used in eqiuimolar amount (500 μM) with the four normal dNTPs in a PCR reaction. The first number at the 5'-end of each sequence indicates how many PCR cycles were allowed in the presence of the analogue(s). The second number identifies different clones.

EXAMPLE 1

Synthesis of dPTP, dKTP and 8-oxodGTP

The 5'-triphosphate derivatives of P and K were prepared by the general procedure described by Ludwig (Ludwig, Acta Biochim. et Biophys. Acad. Sci. Hung. 1981 16, 131). 8-oxodGTP was prepared from dGTP as described (Mo et al., cited above). Purification by anion exchange chromatography (P and K) followed by reverse-phase HPLC (P, K and 8-oxoG) gave the triphosphate samples, judged pure by $^1$H nmr, $^{31}$P nmr and HPLC.

dPTP, dKTP and 8-oxodGTP as Substrates for Taq Polymerase

Using Taq Polymerase and a PCR programme of 30 x (92° C., 1 min; 55° C., 1.5 min; 72° C., 5 min) to amplify a 350 base pair DNA sequence it was found that dPTP could completely replace TTP and yield amounts of product comparable to those obtained using the four normal triphosphates (FIG. 3A), and could replace dCTP to some extent. In contrast, dKTP could replace dATP and dGTP, but only to a limited extent (although such a low level of replacement may well be sufficient to produce a desired level of mutagenesis). When 8-oxodGTP was used, some incorporation into DNA and its extension could be demonstrated by using normal or limiting amounts of dGTP and by compensating with higher concentrations of 8-oxodGTP. FIG. 3B (lanes 1 to 4) shows the PCR product obtained using 500 μM dATP, TTP, dCTP and 8-oxodGTP and decreasing amounts of dGTP (from 50 μM to 6.25 μM). Lanes 5 to 8 show the PCR products obtained using the same conditions but in the absence of 8-oxodGTP.

Kinetics of Incorporation of dPTP by Taq Polymerase

In order to evaluate the performance of dPTP as a substrate for the enzyme Taq polymerase, used in PCR, its rate of incorporation was analysed and compared with TTP (snce initial experiments indicated that its properties best resembled those of this natural triphosphate). FIG. 4A shows the rate of DNA synthesis in the presence of dATP, dCTP and dGTP plus TTP or dPTP. DNA synthesis was measured by the incorporation of [α-$^{32}$P]dCTP using a primed M13 template at 72° C. Incorporation increased linearly in the first 80 seconds when either dPTP or TTP were present. In order to calculate rates of incorporation for different concentrations of substrate, time points were chosen over intervals in which both triphosphate derivatives gave a linear rate of synthesis (FIG. 4B and 4C). Concentrations lower than 50 μM had to be used for dPTP (FIG. 4B) because with higher concentrations the rate of DNA synthesis did not increase linearly with time. For TTP, concentrations between 1.25 and 25 μM were used to obtain measurable differences in rates of incorporation over time (FIG. 4C). The apparent $K_m$ values for TTP and dPTP were determined by analysing the experimental data by the direct linear plot method (Eisenthal and Cornish-Bowden, 1974 J. Biochem. 139, 715). The apparent $K_m$ for dPTP under these experimental conditions was 22 μM, whilst that for TTP was 9.25 μM. The value for dPTP thus compares favourably with those reported in the literature (Kong et al. 1993) for the four natural dNTPs [14 μM–17 μM].

In order to compare the relative efficiencies of insertion of dPTP opposite template adenine and guanine residues respectively, we adopted the procedure of Boosalis et al. (Boosalis et al., 1987 J. Biol. Chem. 262, 14689–14696) for the determination of steady state kinetics using one of two primed synthetic oligonucleotide templates (FIG. 5). The $^{32}$P-labelled primer in each case was extended by the incorporation of dGTP at two positions, followed by dPTP (template 1 and 2), TTP (template 1) or dCTP (template 2). Separation of the products by PAGE followed by quantitation of the radioactivity using a PhosphorImager allowed the determination of the initial velocities (Boosalis et al., 1987). Due to the very high extension rate of Taq polymerase, the kinetic parameters were determined at 55° C. The velocities for the insertion of the particular triphosphate opposite template ($V_{max}$) and $K_m$ values (μM) for particular insertions were determined from non-linear regression fitting to the Michaelis-Menten equation.

Plots of v versus substrate concentration [S] are illustrated for the four possibilities PA, TA, PG and CG in FIGS. 5A–D respectively and the kinetic parameters and catalytic efficiencies ($V_{max}/K_m$) are given in Table 1. The results indicate that dPTP is virtually indistinguishable from TTP in terms of its recognition by Taq polymerase. Furthermore, it is incorporated approximately three times more efficiently opposite template adenine than guanine residues.

$K_m$ values have been reported for 8-oxodGTP with *E.coli* DNA polymerase I Klenow fragment (Purmal et al., 1994) using a procedure analogous to that described here. Values of 63 and 58 μM for insertion opposite C and A respectively were obtained at 37° C. and compare with an average value of approximately 1 μM for the normal dNTPs (Purmal et al., 1994 Nucl. Acids Res. 22, 3930–3935). In addition, the analogue is a substrate for the thermostable Tth DNA polymerase and has been shown to generate A→C transversions at a race of about 1% (Pavlov et al., 1994 Biochem. 33, 4695–4701).

TABLE 1

| Template | Substrate | $V_{max}^{(rel)}$ | $K_m$ (μM) | $V_{max}/K_m$ ($M^{-1}$) | Relative Efficiency |
|---|---|---|---|---|---|
| A | dPTP | 0.86 ± 0.06 | 5.2 ± 1.5 | 16.5 × 10$^4$ | 0.99 |
| G | dPTP | 0.69 ± 0.08 | 12.1 ± 4.8 | 5.7 × 10$^4$ | 0.11 |
| A | TTP | 1.02 ± 0.11 | 6.1 ± 1.5 | 16.7 × 10$^4$ | 1.00 |
| G | dCTP | 1.01 ± 0.09 | 2.03 ± 0.68 | 49.8 × 10$^4$ | 1.00 |

Mutation Frequencies Induced by dPTP, 8-oxodGTP and Their Mixture

In order to investigate the mutations resulting when dPTP or 8oxodGTP was used in DNA synthesis reactions, PCR reactions were set up in which dPTP was added in equimolar concentrations to the four normal dNTPs. The DNA was amplified for a variable number of cycles and, in order to eliminate the incorporated base analogues, an aliquot of the amplified DNA was used as template in a second PCR amplification in which only the four normal dNTPs were used. The PCR product was subsequently cloned, and some of the clones sequenced (in this way, the pattern of mutation was not influenced by the DNA repair mechanisms of the *E. coli* host). FIG. 6 shows the accumulation of point mutations in DNA amplified in the presence of equimolar concentrations of the four normal dNTPs and dPTP (□), or 8oxodGTP (◊) or dPTP+8-oxodGTP (○). The data illustrate three points: (i) that very high mutation frequencies can be obtained after 30 cycles of PCR and that these frequencies are higher than those reported by other methods; (ii) that the number of mutations per clone can be controlled by cycle number (FIG. 6); and (iii) mutational yield is more than additive when a combination of the two analogues is used.

Mutation Patterns Generated by dPTP, 8-oxodGTP and Their Mixture

Figure 1:
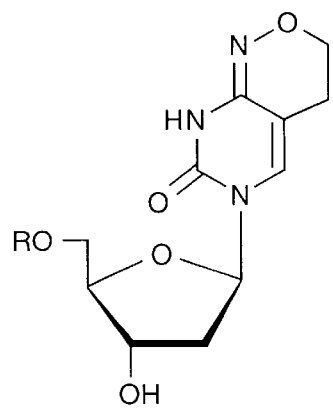
FIG. 1 shows the structural formulae of various compounds 1–6.
Figure 1:
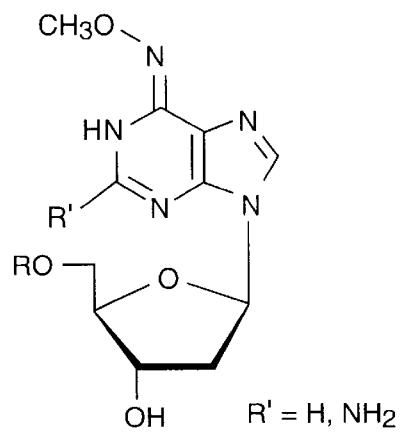
Figure 1:
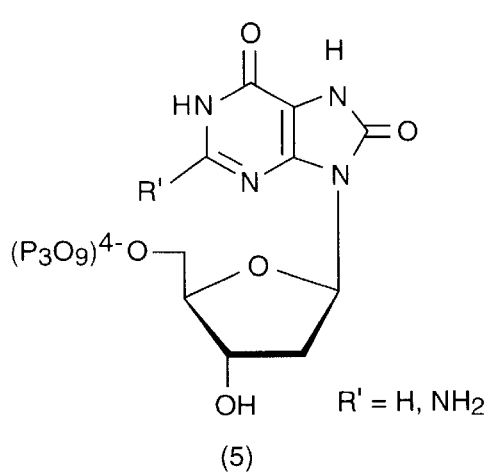
Figure 1:
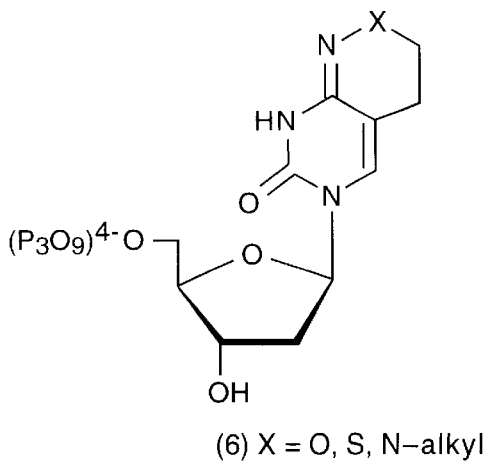
Figure 2:
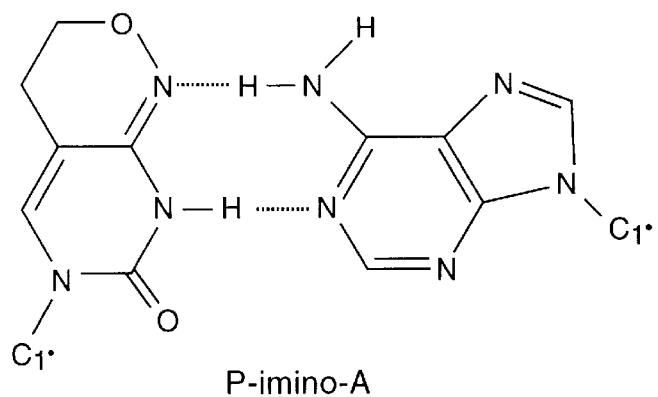
FIG. 2 illustrates schematically the base-pairing of P with adenine and guanine, the ambiguity of which is partly the basis for a powerful transition mutagenic effect.
Figure 2:
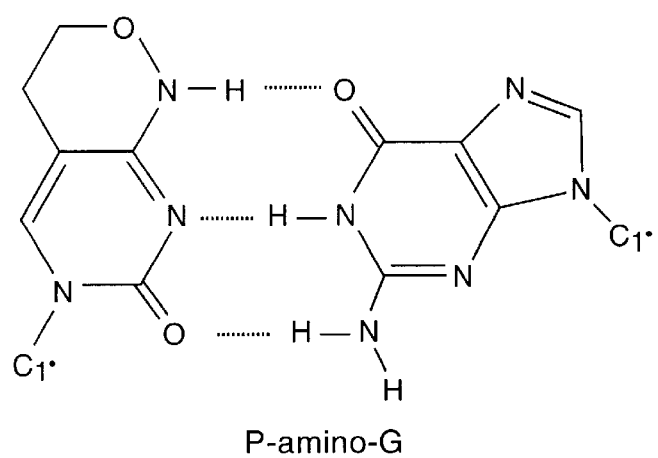
Figure 2:
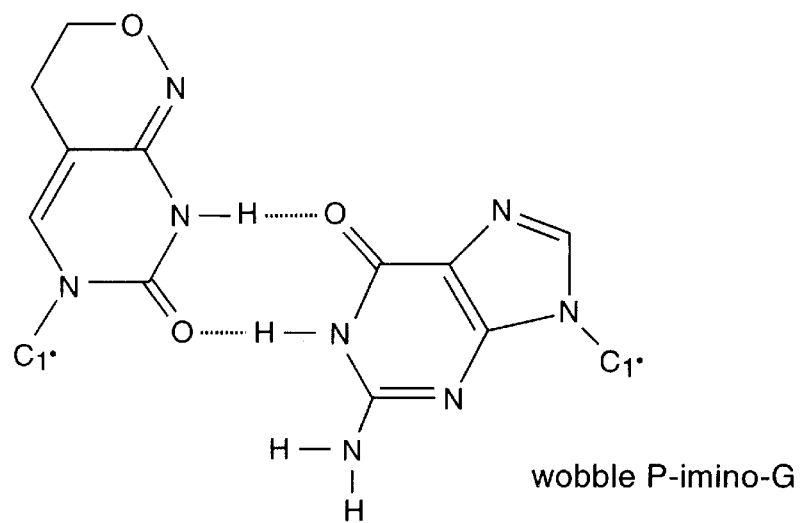

Since the base pairing potential of the nucleosides dP and 8-oxodG is different (dP pairs with adenine or guanine—Kong & Brown Nucl. Acids Res. 1989, cited above, as illustrated in FIG. 2) and 8-oxodG pairs with adenine or cytosine (Pavlov et al., cited above;, Kuchino et al. Nature 1987 327, 77; Monya, Proc. Natl. Acad. Sci. USA 1993 90, 1122) the inventors analysed the nucleotide changes produced by the two analogue triphosphates and their combination. These results are shown in FIGS. 7A–7C and are expressed as a percentage of all mutations sequenced. The figures illustrate that dPTP produces four transitions (A→G, T→C, G→A and C→T). Two transitions (A→G and T→C) occur at higher frequency than the other two (G→A and C→T). This results from a preference for insertion of dPTP opposite to adenine in the template sequence. The ambivalent base-pairing potential of P (as illustrated in FIG. 2) results in the generation of transition mutations either during the incorporation of the dPTP or in its replication subsequent to incorporation. 8-OxodGTP produces two transversions (A→C and T→G) resulting from the analogue being incorporated in place of TTP on either strand and subsequently directing the insertion of dCTP as observed previously (Pavlov et al., Mo et al., and Kuchino et al., all cited above). The use of both analogues in a single DNA synthesis reaction results in the generation of mutations produced by the two base analogues with comparable frequencies. Moreover, some additional mutations (e.g. C→G) are observed. The respective types of nucleotide changes induced by dPTP and 8-oxodGTP have a consequential effect on the amino acid sequence of the mutants. Sequencing of 12 mutant clones obtained in the presence of dPTP and equimolar concentrations of the four normal dNTPs showed that 40 out of 43 codons present in the test sequence were mutated to alternative ones (FIGS. 8A–8D). The sequences of 8 mutant clones obtained in the presence of 8-oxodGTP and equimolar concentrations of the four normal dNTPs showed that 18 codons were replaced (FIGS. 9A–9D). It is worth noting that while both analogues can lead to certain point mutations, other mutations are only produced by dPTP and 8-oxodGTP together, demonstrating that the use of appropriate mixtures of triphosphate derivatives of nucleoside analogues represents a powerful procedure for the introduction of random mutations into DNA (FIGS. 11a1–11C5).

Figure 11A:
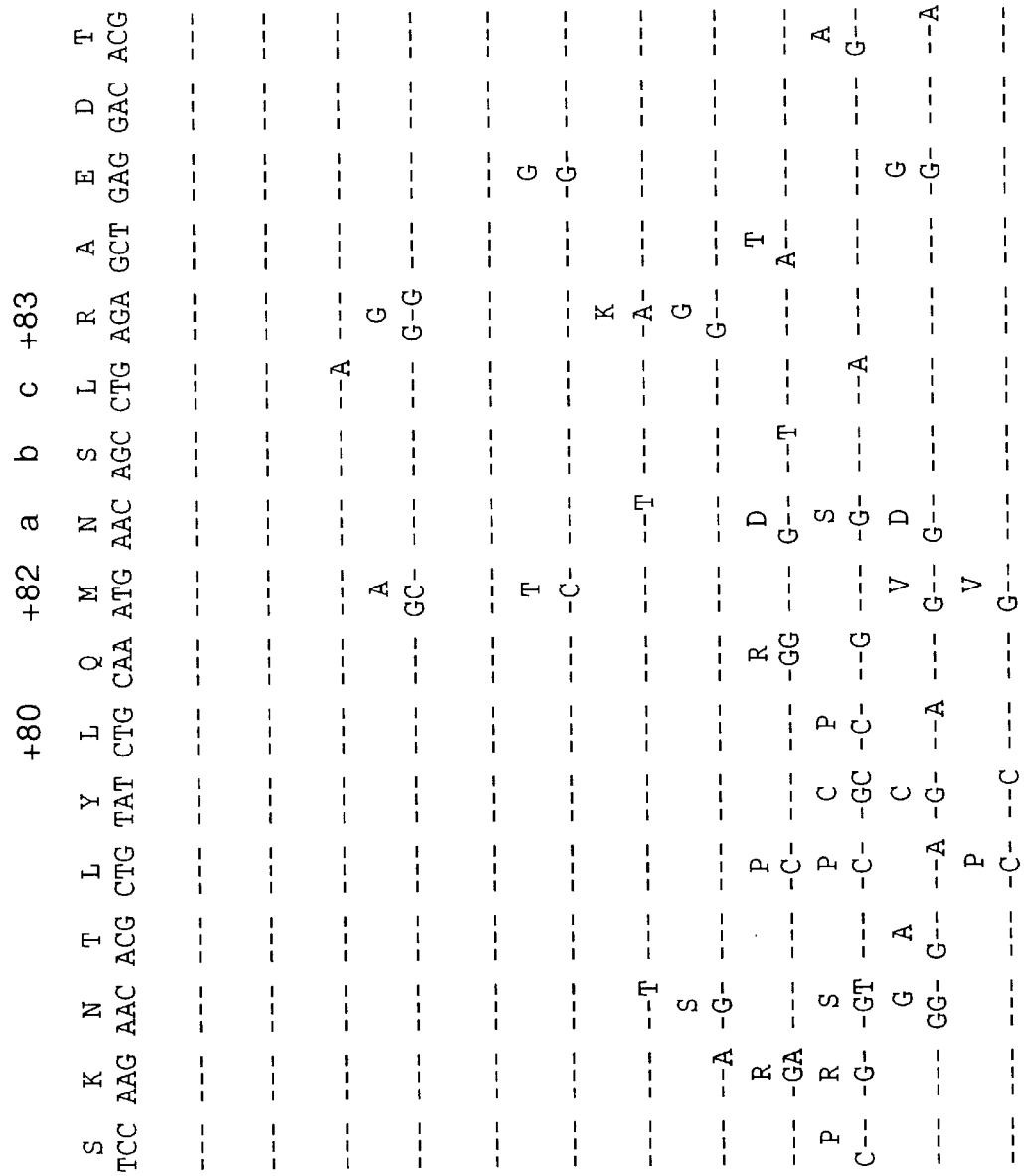
Figure 11C3:
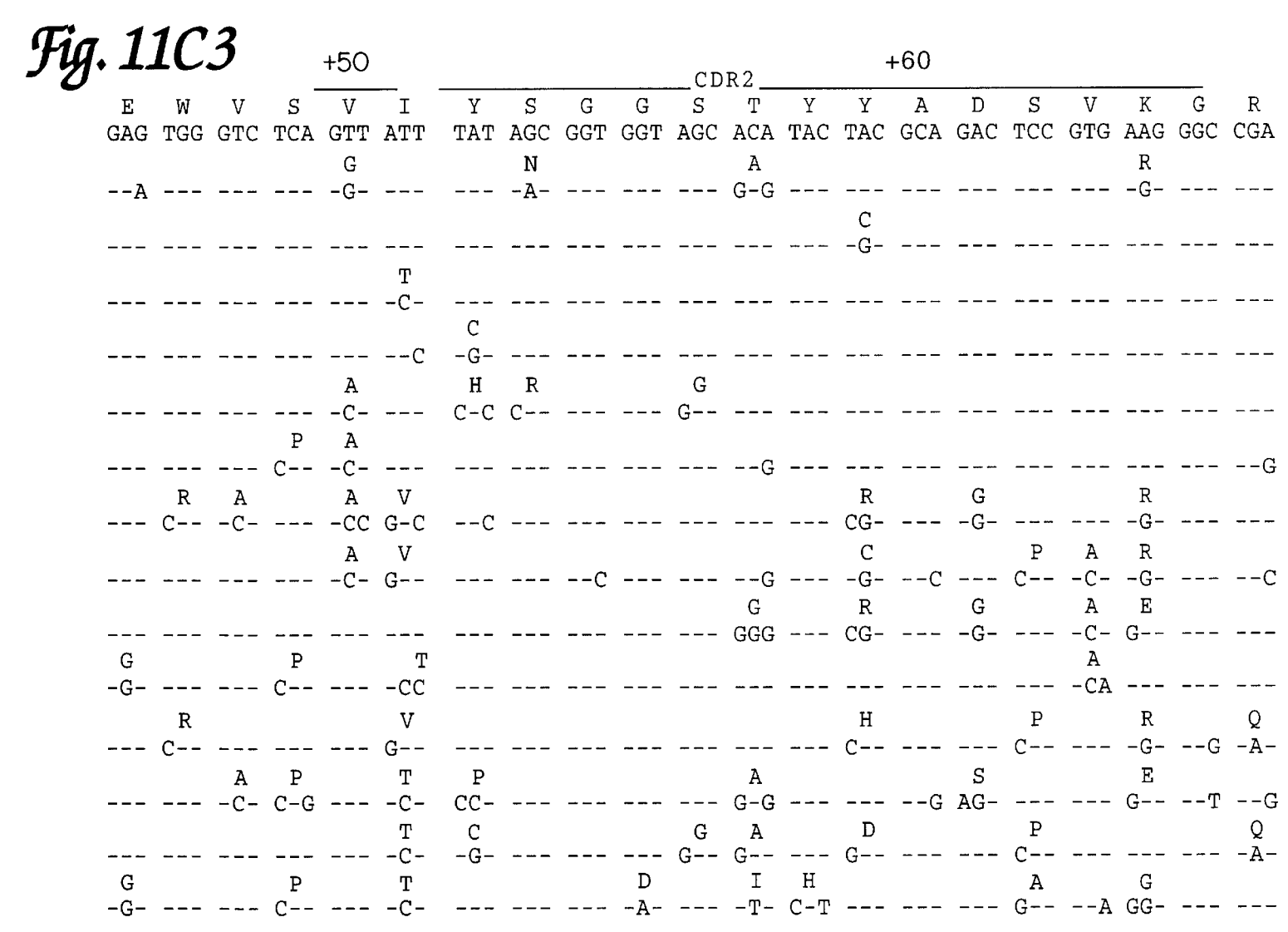
Figure 11C5:
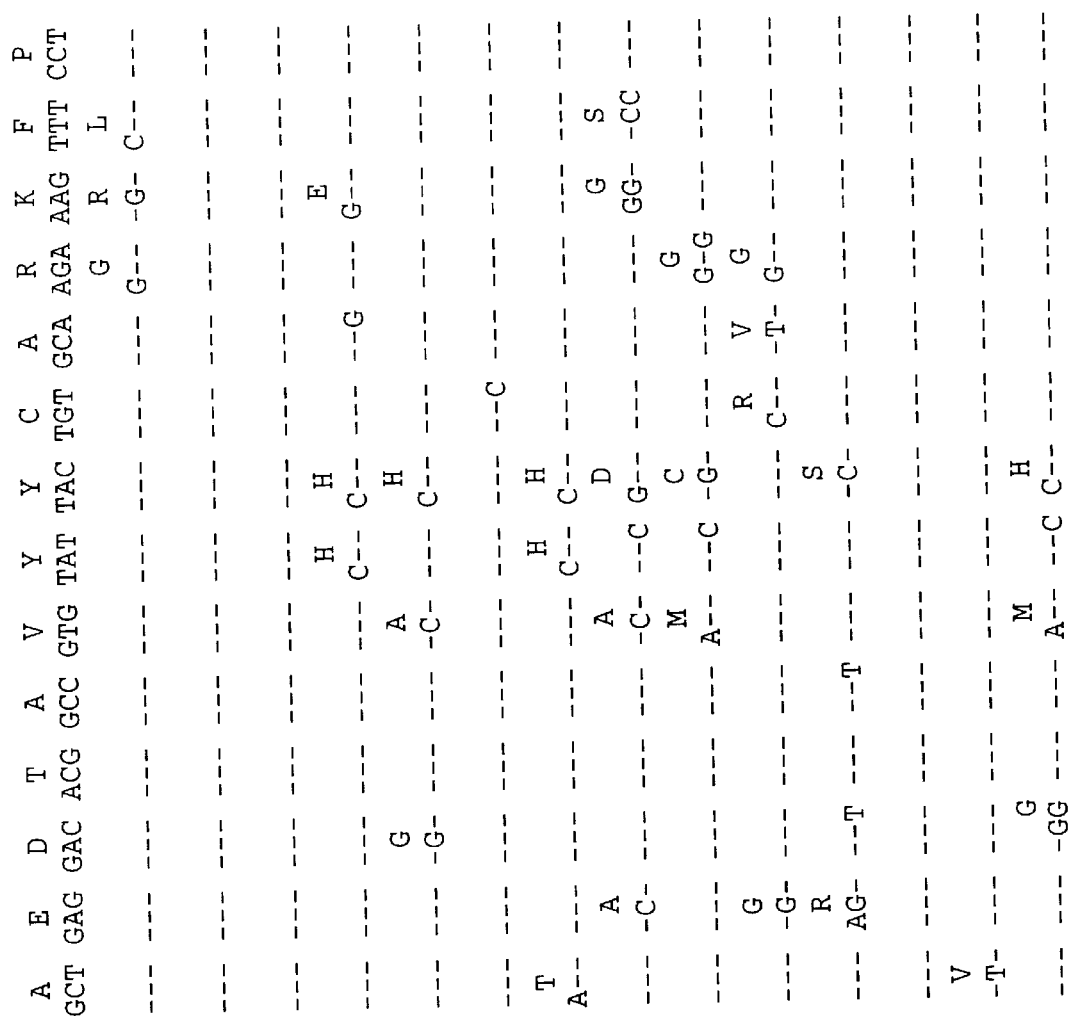

FIGS. 11a2–11C5 shows the results of a series of mutagenesis experiments in which the following equimolar nucleotide mixtures were used: the four normal dNTPs and dPTP (FIG. 11A); the four normal dNTPs and 8-oxodGTP (FIG. 11B); the four normal dNTPs, dPTP and 8-oxodGTP (FIG. 11C). Similar experiments were carried out on a second target gene with comparable results (data not shown). DNA amplification reactions were carried out for variable number of cycles, as indicated in FIGS. 11A–11C by the number preceding the point in the clone designation. The data show that a significant number of point mutations are generated in the target gene under the three experimental conditions tested, although dPTP clearly proved to be a much more efficient mutagen than 8-oxodGTP. The data also clearly show that the number of mutations increased as a function of the number of cycles used for the DNA amplification reaction. When the frequency of mutations was plotted against the number of PCR cycles (FIG. 6) a linear relation was apparent both in the case of 8-oxodGTP and for the mixture of dPTP and 8-oxodGTP at least up to 30 cycles. In the case of dPTP the relation was linear for the first 20 cycles. For low numbers of cycles, the combination of the two triphosphate analogues appeared to produce a total number of mutations lower than that produced by dPTP alone, although the DNA produced in such reactions contained both dP-induced and 8-oxodG-induced mutations (see below).

Although the clones sequenced after different numbers of PCR cycles were obtained from separate PCR reactions, it is interesting to note that bases at particular positions were mutated more frequently than others. The mutations nevertheless appeared to accumulate over the entire gene sequence.

The total number of bases sequenced in the cloned inserts and the mutations generated by dPTP, 8-oxodGTP and their combination are listed in Table 2. The pattern of mutations produced by dPTP, 8oxodGTP and their combination is shown in FIGS. 7A–C. Thus of the mutations generated by dPTP 46.6% are A→G, 35.5% were T→C, while G→A were 9.2% and 8% were C→T. The major mutational events (A→G and T→C transitions) result from the preferential incorporation of dPTP opposite A in either strand and subsequent pairing of the incorporated P with G. To a lesser extent, the incorporation of dPTP opposite G in either strand and subsequent pairing of P with A (G→A and C→T transitions) also occurs. In addition to the four transitions, mentioned above, one T→G and two A→T transversions were found out of 4093 bp sequenced (see FIGS. 7A–C).

TABLE 2

Numbers and types of mutation produced using dPTP, 8-oxodGTP in PCR

| Mutagenic dNTP | Bases sequenced | Number of point mutations | | |
|---|---|---|---|---|
| | | total | coding | silent |
| dPTP | 4093 | 384 | 318 | 66 |
| 8-oxodGTP | 5463 | 91 | 65 | 16 |
| dPTP & 8-oxodGTP | 3751 | 387 | 334 | 53 |

In the mutants generated with 8-oxodGTP two types of transversion mutations were present: A→C (38.8%) and T→G (59%). These derive from the misincorporation of 8-oxodGTP opposite A in either template stand (Shibutani et al., 1991 Nature 349, 431–434). One C→A transversion was found out of 5463 bp sequenced. This mutation might be due to incorporation of 8-oxodGTP opposite C in the template followed by misincorporation of dATP opposite template 8-oxodG during subsequent replication. This mutagenic mechanism for 8-oxodGTP has been previously reported to occur when 8-oxodGTP completely substitutes for dGTP (Cheng et al., 1992 J. Biol. Chem. 267, 166–172). A very small number of additional mutations were also found: two A→G transitions and one G→A transition.

From clones mutagenised with the combination of dPTP and 8-oxodGTP together, the pattern of mutations observed under these conditions is shown in FIGS. 9A–D. All types of transition and transversion mutations which were expected from the combination of the two triphosphate analogues were observed although their respective frequencies were slightly different from those predicted based on the combined frequencies of dPTP and 8-oxodGTP mutations. The mixture of the two analogues also increased the frequency of additional mutations ($1 \times 10^{-3}$).

No insertions and a single two-nucleotide deletion were found using either analogue over a total of 13.307 bp sequenced.

The effects of the four transition mutations induced by dPTP and the two transversion mutations induced by the 8-oxodGTP were also analysed at the codon level. FIGS. 10A–D show the results of this analysis. The figure groups amino acids into five classes: glycine, non polar, polar, positively charged and negatively charged and shows the codon changes resulting from dPTP mutagenesis (circles), 8-oxodGTP mutagenesis (squares) and their combination (triangles). Codon changes resulting from a single base substitution are shown as full symbols, those resulting from a double substitution are shown as open symbols.

In spite of the clear bias in the mutations induced by dPTP and 8-oxodGTP (FIGS. 7A–C), the use of these analogues or their combination allowed extensive codon changes to be achieved. The two genes used as model templates contained 51 out of the possible 64 codons (codons not present in either gene are marked with an asterisk in FIG. 10). Of the 51 codons present, 50 were mutated by dPTP or 8-oxodGTP or by their combination.

Of 224 codon changes which were found one or more times in the database, 49 were silent, 66 changed the amino acid to another of the same class, 105 changed the amino acid to one of a different class and 4 led to termination codons.

These results thus demonstrate that a broad spectrum of amino acid substitutions can be generated by dPTP and/or 8-oxodGTP mutagenesis.

Experimental Details

6(2-Deoxy-β-D-erythropentofuranosyl)-3,4dihydro-8H-pyrimido-[4,5-c][1,2]oxazine-7one 5'-triphosphate, Triethylammonium salt. (dPTP) (structure 2)

The P nucleoside (Kong Thoo Lin & Brown 1989, cited previously)—54 mg, 0.2 mol—was dried in vacuo over $P_2O_5$ at 80° C. overnight then suspended in dry trimethylphosphate (0.5 mL) under argon. The flask was cooled in an ice-bath whilst phosphoryl chloride (21 µL) was injected with stirring. After stirring in the ice bath for 45 mins., a vortexed mixture (0.5 M in anhydrous DMF, 1.0 mL) of bis-tributylammonium pyrophosphate (Ludwig & Eckstein J. Org. Chem. 1989 54, 631), tributylamine (0.2 mL) and anhydrous DMF (0.4 mL) was added with rapid stirring in ice, followed after 10 mins by triethylammonium bicarbonate solution (pH 7.5, 0.1 M, 20 mL). After 1 hr, the sample was diluted with water (20 mL) and applied to a column of Sephadex A25 (diam. 25×330 mm) containing 0.05 M triethylammonium bicarbonate solution. The column was eluted with a linear gradient of triethylammonium bicarbonate (1.5 L each of 0.05–0.8 M) at 4° C. The 5'triphosphate of P eluted between 0.48 and 0.54 M buffer. The triphosphate-containing fractions were combined and evaporated and the residue coevaporated with methanol then dissolved in water (10 mL). The product was purified further by reverse phase HPLC using a Waters 7.8×300 mm C18 semi-preparative column and a linear gradient of 0–4.5 % acetonitrile in 0.1 M triethylammonium bicarbonate pH 7.5 with flow rate of 2.5 mL/min. Appropriate fractions were combined, evaporated and residual buffer removed by coevaporation with methanol to afford the pure triphosphate as the tetrakistriethylammonium salt (253 $A_{260\ at\ pH}$ 7, 0.067 mmol, 34%). δ($D_2O$) −9.57 (d, γ-P), −10.34(d, α-P), −22.02 (t, β-P). Approx. HPLC retention time=18.5 min.

2-Amino-9-(2-deoxy-β-D-erythropentofuranosyl)-6-methoxyaminopurine 5'-triphosphate, Triethylammonium salt. (dKTP) (structure 4, where R'=$NH_2$)

29.6 mg (0.1 mol) of the K nucleoside (Brown & Kong Thoo Lin 1991, cited previously) was dried in vacuo over $P_2O_5$ at 80° C. overnight then suspended in dry trimethylphosphate (0.25 mL) under argon. The flask was cooled in an icebath whilst phosphoryl chloride (12 µL) was injected with stirring. After stirring in the ice bath for 70 mins., a well-vortexed mixture (see Ludwig & Eckstein, cited above) of bis-tributylammonium pyrophosphate (0.5 M in anhydrous DMF, 0.5 mL), tributylamine (0.1 mL) and anhydrous DMF (0.2 mL) was added with rapid stirring, followed after 7.5 mins by triethylammonium bicarbonate solution (pH 7.5, 0.1 M, 5 mL). After 1 hr, the sample was diluted with water (30 mL) and applied to a column of Sephadex A25 (diam. 26×220 mm) containing 0.05 M triethylammonium bicarbonate solution (pH 7.5). The column was eluted with a linear gradient of triethylammonium bicarbonate (1 L each of 0.05–0.8 M) at 4° C. The desired 5'triphosphate of K eluted between 0.50 and 0.68 M buffer. The triphosphate containing fractions were combined and evaporated and the residue coevaporated with methanol then dissolved in water (10 mL). The product was purified further by reverse phase HPLC using a Waters 7.8×300 mm C18 semi-preparative column and a linear gradient of 0–4.5 % acetontrile in 0.1M triethylammonium bicarbonate pH 7.5. Appropriate fractions were combined, evaporated and residual buffer removed by coevaporation with methanol to afford the pure triphosphate as the tetrakistriethylammonium salt (446 $A_{260}$ at pH 7, 0.043 mmol, 43%). $\delta(D_2O)$ –10.37 (d, γ-P), –10.89 (d, α-P), –23.62 (t, β-P). Approx. HPLC retention time— 14.7 min.

2'-Deoxy-8-hydroxyguanosine 5'-triphosphate, Triethylammonium salt (8-oxodGTP) (structure 5, where R'=NH$_2$)

This compound was prepared essentially according to Mo et al. (cited previously). Thus, dGTP (trisodium dihydrate, 58.48 mg, 96 μmol) in 100 mM sodium phosphate (8 mL) containing 30 mM ascorbic acid and 100 mM hydrogen peroxide was incubated at 37° C. for 4 hr. in the dark. The product was purified directly by reverse phase HPLC using a Waters 19×300 mm C18 preparative column and a linear gradient of 015 % acetonitrile in 0.1M triethylammonium bicarbonate pH 7.5 with a flow 7.5 mL/min. Appropriate fractions were combined, evaporated and residual buffer removed by coevaporation with methanol to afford the pure triphosphate as the tetrakistriethylammonium salt. The absorbance spectrum was identical to that described by Mo et al., (cited previously) and by Wallace et al., (Nucl. Acids Res. 1994 22, 3930)—(12.3 $A_{244}$, 10.3 $A_{293}$ at pH 7, 5.2 μmol, 5.4%). $\delta(D_2O)$ –9.68 (d, γ-P), –10.46 (d, α-P), –22.40 (d, β-P), Approx. HPLC retention time=27.9 min, dGTP 26.0 min.

The foregoing section comprises a detailed discussion as to how a particular novel compound (dPTP), within the scope of the invention may be synthesised. It will be clear to those skilled in the art, with the benefit of the disclosure contained herein, how other compounds within the scope of the invention may be made. For example, to prepare the ribonucleotide equivalent (rP) of dP, essentially the same synthetic route could be employed (using appropriate starting materials), using triacetylribofuranosyl chloride (for improved solubility) instead of the di-p-toluoyl 2-deoxyribosyl chloride compound described above.

Mutagenesis

For mutagenesis experiments, 10 fmoles of template DNA were amplified using 0.5 μl of AmpliTaq polymerase (5 U/μl, Applied Biosystems) in a 20 μl reaction containing the appropriate sense and antisense polymers at 0.5 μM, 2 mM MgCl$_2$, 10 mM Tris-HCl pH8.3, 50 mM KCl, 1 g/l gelatine and dATP, dCTP, dGTP, TTP, dPTP and/or 8-oxodGTP, each at 500 μM. After various cycles (92° C. for 1 min, 55° C. for 1.5 min, 75° C. for 5 min), 1 μl of the amplified material was used in a second PCR in which the same conditions as above were used except that no dPTP or 8-oxodGTP were added to the reaction mixture. The product of the second PCR was digested with BstEII and PstI and cloned into M13VHPCR1 vector (Jones et al., 1986 Nature 321, 522–525). Sequence analysis of single stranded DNA prepared from single phage isolates was performed using Sequenase Version 2 (United States Biochemicals, Cleveland, Ohio) according to the manufacturer.

EXAMPLE 2

Random Mutagenesis and Selection of an Enzyme with Improved Catalytic Activity

In order to investigate the potential of the mutagenesis method in experiments of in vitro directed molecular evolution, the enzyme TEM-1 β-lactamase was used as a model system.

β-lactamases are responsible for bacterial resistance to β-lactam antibiotics such as ampicillin and cephalosporins by catalysing the hydrolysis of the β-lactam ring and generating an inactive product. TEM-1 is a particularly attractive model system because a very efficient chemical selection for improved function can be applied. Thus the model allows us the assessment of the potential of the mutagenesis method per se, without the possible limitations due to insufficient resolution of the screening/selection technique.

In this experiment we set to improve the hydrolytic activity of the enzyme TEM-1 β-lactamase on the poorly hydrolysed substrate cefotaxime [minimum inhibitory concentration (MIC)=0.02 μg/ml] by repeated rounds of random mutagenesis and selection on increasing concentrations of the antibiotic. The best mutants selected in the first round are subjected to a second round of mutagenesis and selection in the presence of higher concentration of antibiotic. A stepwise improvement of the efficiency of TEM-1 hydrolytic activity is attained by progressively increasing the selective pressure.

The wild type TEM-1 gene from the plasmid pBR322 was used as a template for PCT amplification in the presence of dPTP and 8-oxodGTP in addition to the four normal dNTPs. The pool of mutants generated was cloned in the vector pBC KS$^+$ and the library of mutants transformed in E. coli by electroporation. The transformed bacteria were then plated on increasing concentrations of the antibiotic cefotaxime. Bacteria growing on a concentration of cefotaxime higher than the MIC of 0.02 μg/ml carry a mutant of TEM-1 with improved hydrolytic activity on this substrate. Selected mutant were analysed by sequencing and the results of the first round of mutagenesis and selection are shown in Table 3A. A different number of cycles of the mutagenic PCT was used to generate four independent libraries of mutants (libA, libB, libC and libD) each characterised by a different frequency of mutation (0.3% for libA, 0.3% for libB, 1.8% for libC and 6.3% for libD), as determined by sequence analysis of unselected clones. An aliquot of each library (~5×10$^4$ cfu) was plated on 0.2 μg/ml cefotaxime (10 times the MIC) and inspection of the plates after incubation at 37° C. for 24h revealed several colonies (>50 colonies/plate). Table 3A shows the results of the sequence analysis of selected clones growing on these plates. Asterisks indicate silent mutations; aminoacid numbering is according to Ambler et al., (Biochem. J., 1991 266, 3186). Underlined residues belong to the leader peptide. Most of the selected clones contain multiple nucleotide substitutions generating both silent and coding mutations. Interestingly, mutations at particular positions (see for example L21P, V23A, G238S, E240G etc.) were found several times in independently generated libraries.

The high number of colonies growing on 0.2 μg/ml cefotaxime prompted us to look for mutants able to grow on even higher concentration of antibiotic. All colonies were scraped off the plates, dissolved in broth and an aliquot from each library was plated on medium containing 2 μg/ml cefotaxime. Plates were incubated at 37° C. for 24 h and then inspected for colony growth. Selected clones were sequenced and the results are shown in Table 3B. All the mutants sequenced, except one, contained a G238S mutation. The only exception is a clone containing an R164S mutation. Both these mutations have been found in natural isolates of TEM-1 β-lactamase showing improved hydrolytic activity on cefotaxime. Clone 6a contains R241H and D252G mutations in addition to G238S. When its enzymatic activity was compared with that of the single mutant G238S it appeared to be at least ten times higher, with colonies growing on >20 μg/ml.

A
Clones selected on 0.2 μg/ml cefotaxime

| | 3 | 15 | 21 | 23 | 164 | 192 | 199 | 202 | 206 | 207 | 208 | 215 | 218 | 232 | 234 | 238 | 240 | 241 | 251 | 252 | 253 | 254 | 266 | 280 |
|---|---|---|---|---|---|---|---|---|---|---|---|---|---|---|---|---|---|---|---|---|---|---|---|---|
| wt | I | F | L | V | R | K | L | A | Q | L | I | K | G | A | K | G | E | R | L | D | G | K | T | A |
| 1a | | | | | | | | | | | | | | | | | S | | | | | | | |
| 2a | | | | | | | | | | | | | | | | | | G | | | | | | |
| 3a | | | | | | | | | | | | | | | | | | G | | | Q | | | |
| 4a | | P | A | | | | | | | | | | | | | | S | | * | N | | A | | |
| 5a | | | | | | | | | | | | | | | | | | G | * | | * | Q | A | |
| Ic | T | * | | | * | P | V | * | S | V | E | | | * | * | | | | | | | | | |
| 2c | | * | P | A | | | | | | | | | | | | | S | | * | N | | A | | |
| 3c | | * | P | A | | | | | | | | | | | | | S | | * | N | | A | | * |
| Id | | | | | | | | | | | | | | | | | G | | | | | | | |

B
Clones selected on 2 μg/ml cefotaxime

| | 3 | 15 | 21 | 23 | 164 | 192 | 199 | 202 | 206 | 207 | 208 | 215 | 218 | 232 | 234 | 238 | 240 | 241 | 251 | 252 | 253 | 254 | 266 | 280 |
|---|---|---|---|---|---|---|---|---|---|---|---|---|---|---|---|---|---|---|---|---|---|---|---|---|
| wt | I | F | L | V | R | K | L | A | Q | L | I | K | G | A | K | G | E | R | L | D | G | K | T | A |
| 6a | | | | | | | | | | | | | | | | | S | | U | | G | | | |
| 7a | | | | | | | | | | | | | | | | | S | | | | | | | |
| Ib | | | | | | | | | | | | | | | | | S | | | | | | | |
| 4c | | | | | | | | | | | | | | | | | S | | | | | | | |
| 5c | | | | | S | | | | | | | | | | | | | | | | | | | |
| 2d | | | | | | | | | | | | | | | | | S | | | | | | | |

These preliminary results indicate that random mutagenesis of DNA by PCT using triphosphate analogues is an effective way to generate large pools of protein mutants among which it is possible to select variants showing improved performance. The method we propose generates very efficiently large numbers of mutants and allows control over the frequency of mutation. As a consequence, it was possible to select enzyme mutants with improved catalytic activity by screening a relatively small number of variants ($\sim 10^5$), well within the average library size. Moreover, the possibility to control the frequency of mutation and to introduce, on average, more than one nucleotide substitution per gene, allowed us to isolate in a single step of mutagenesis and selection a triple mutant in which the mutations appear to have cooperative effect on the efficiency of TEM-1 hydrolytic activity.

Discussion

Further developments of the approach described herein are envisaged. Firstly, modification of dPTP to produce a closely related analogue which displays a tautomeric constant closer to unity would adjust the balance between all four possible transition mutations. The second concerns the ratio of transition versus transversion mutations in experiments in which both the dPTP (or related) analogue and 8-oxodGTP are used in combination. In the experiments reported here, both analogues were used at the concentration of 500 μM but the higher rate of incorporation and/or extension of dP led to a higher frequency of dP-induced mutations. It should be possible to obtain comparable numbers of transitions and transversions from mutagenesis reactions in which the concentrations of dPTP and 8-oxodGTP are adjusted in order to compensate for their different kinetics. Finally, it is clear that six transversion mutations (C→G, G→T, T→A, A→T, C→A and G→C) either are not produced by the dNTP mixture, or else they are produced at very low frequencies. Other analogues therefore, such as $O^2$-ethylthymidine triphosphate which induces A→T transversions, albeit at a low frequency, (Singer et al. 1989) could be used in order to extend the range of transversion mutations.

While in vitro point mutagenesis followed by selection clearly aims to mimic an important aspect of protein evolution, it is clear that nature's strategy of protein engineering equally relies on a variety of other processes such as gene insertions, deletions, duplication and recombination. Procedures are being developed which aim to reproduce these events in vitro and harness their potential for protein engineering. In one such procedure, gene fragments obtained by DNaseI treatment are reassembled by PCR in a process that promotes random recombination (Stemmer, 1994 Proc. Natl. Acad. Sci. USA 91, 10747–10751). The effectiveness of this approach has been clearly illustrated by its application in the engineering of β-lactamase mutants, one of which, when expressed in *E. coli,* showed a 32,000 fold increase in minimum inhibitory concentration compared to wild-type enzyme (Stemmer 1994 Nature 370, 389–391). It is of interest, however, that the sequence of the improved mutant only contained 5 point mutations compared to the wild-type enzyme. This shows that Stemmer's protocol is accompanied by an appreciable rate of point mutagenesis and that, at least in the β-lactamase example, such point mutations are entirely responsible for the maturation of the enzyme in the absence of bona fide recombination. The results, nevertheless, reinforce the concept that point mutagenesis is a powerful approach for protein engineering in vitro and suggest that recombination coupled with point mutagenesis may have a special potential for engineering new proteins from series of homologous genes.

Previous DNA mutagenesis protocols typically resulted in relatively low mutational rates. The procedure described here, however, can lead to a frequency of nucleotide substitutions approaching 1 in 5 after 30 cycles of DNA amplification. This clearly raises the issue of an optimal mutational load for protein engineering.

It seems reasonable to suggest that the lower limit of an efficient random mutagenesis protocol may aim at introducing, on average, one amino acid change per sequence but this may well be sub-optimal. While a very large number of simultaneous substitutions would clearly destroy protein stability, studies with several model systems suggest that relatively few amino acids positions are critical for function and stability.

In T4 lysozyme, for example, substitution of each amino acid (except for the initiator methionine) with 13 different amino acids has shown that more than half the positions tolerated all substitutions (Rennell et al., 1991 J. Mol. Biol. 222, 67–87). Furthermore, out of 2015 mutations, only 173 were seriously deleterious and these were confined to 53 out of 163 positions (Rennell et al., 1991). Studies on the γ repressor also demonstrated the fact that numerous substitutions in the core of the protein are tolerated (Lim et al., 1991 J. Mol. Biol. 219, 359–376).

Although these studies do not address directly the effect of multiple random mutations, they suggest, nevertheless, that these would not invariably result in the loss of protein function, an argument reinforced by the results of studies on somatic hypermutation of antibody genes. Antibodies isolated in secondary or tertiary responses contain a considerable number of replacement mutations (see Berek & Milstein 1987 Immunol. Rev. 96, 23–41). In cases in which the role of individual substitutions has been analysed, it appeared that only a few mutations played a role in affinity maturation (for example 3 out of 19 amino acids in the anti-p-azophenylarsonate antibody) (Sharon 1990 Proc. Natl. Acad. Sci. USA 87, 4814–4817), yet the VH and VL domains appear to tolerate as substitution rates approaching 1 in 10.

The procedure described here may allow the optimal mutational load for protein engineering to be addressed experimentally since this can now be readily controlled and libraries of protein mutants carrying different numbers of substitutions can be constructed. These studies should assist exploring the potential of the mutagenesis/selection approach for protein engineering.

Finally, the relationship of the present invention to combinatorial oligonucleotide chemistry should be mentioned. In the latter, a wide variety of short (n) repertoires, generally of large sequence content (e.g. $4^n)^+$ can be synthesised. Essentially all possible sequence isomers are formed and effective rounds of selection have to be applied in a variety of formats to identify the sequence of interest. Typically, in the present approach an already functional DNA sequence is amplified under a variable mutational pressure and the products then cloned. The mutational frequencies observed, as related to PCR cycle number, were derived from a few tens of randomly-picked colonies. These mutation frequencies presumably hold for all the clones carrying the insert. Thus the number of mutant inserts sequenced represents a very small fraction of the total formed in each amplification process. Routine selection methods akin to those used with the large synthetic repertoires should demonstrate the applicability of the present invention to the problems discussed above.

We claim:
1. A compound having the structure:

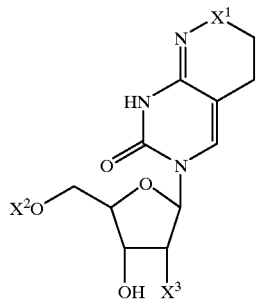

where $X^1$ is selected from the group consisting of O, S, N-alkyl, $N^+$-dialkyl and N-benzyl; $X^2$ is selected from the group consisting of triphosphate $(P_3O_9)^{4-}$, diphosphate $(P_2O_6)^{3-}$ and thiotriphosphate $(P_3O_8S)^{4-}$; and $X^3$ is selected from the group consisting of H, $NH_2$, F and OR, where R is H, methyl, allyl or alkaryl.

2. A compound according to claim 1, wherein $X^1$ is O.

3. A compound according to claim 2, wherein, $X^2$ is triphosphate, and $X^3$ is H or OH.

4. A method of mutating a nucleic acid sequence, comprising replicating a template sequence in the presence of a nucleoside triphosphate analogue in accordance with claim 1, so as to form non-identical copies of the template sequence having one or more nucleoside phosphate analogue residues.

5. A method according to claim 4, comprising replicating a template sequence in the presence of deoxyP triphosphate, so as to form non-identical copies of the template sequence having one or more dP nucleotide residues.

6. A method according to claim 4, further comprising wherein the template sequence is replicated in the presence of one or more additional nucleoside triphosphates.

7. A method according to claim 4, further comprising wherein the template sequence is replicated in the presence of a second compound having the structure:

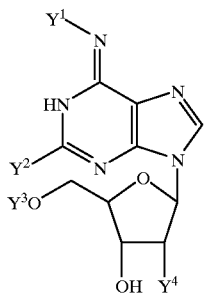

where $Y^1$ is selected from the group consisting of OH, O-alkyl, $NH_2$ and $N(Alkyl)_2$; $Y^2$ is selected from the group consisting of H and $NH_2$; $Y^3$ is selected from the group consisting of triphosphate $(P_3O_9)^{4-}$, diphosphate $(P_2O_6)^{3-}$ and thiotriphosphate $(P_3O_8S)^{4-}$; and $Y^4$ is selected from the group consisting of H, $NH_2$, F and OR, where R is H, methyl, allyl or alkaryl.

8. A method according to claim 4, further comprising wherein the template sequence is replicated in the presence of at least one member of the group consisting of 2'-deoxy-8-hydroxyguanosine 5'-triphosphate, 2-amino-9-(2-deoxy-β-D-erythropentofuranosyl)-6-methoxyaminopurine 5'-triphosphate, and $O^2$-ethylthymidine triphosphate.

9. A method according to claim 4, further comprising the step of replicating the non-identical copies of the template sequence in the presence of the four normal dNTPs, but in the absence of analogues thereof, to form further non-identical copies of the template sequence comprising only the four normal deoxynucleotides.

10. A method according to claim 4, wherein the replication of the template sequence, and/or the replication of the non-identical copies thereof, is achieved by means of PCR.

11. A method according to claim 4, further comprising wherein the template sequence is replicated in the additional presence of the four normal deoxynucleotides.

12. A method according to claim 5, wherein the template sequence is replicated in the presence of 1 μM to 600 μM 6-(2-deoxy-β-D-erythropentofuranosyl)-3,4 dihydro-8H-pyrimido [4,5-c][1,2]oxazine-7-one 5' triphosphate.

13. A method according to claim 5, wherein the template sequence is replicated in the presence of 1 μM to 600 μM 2'-deoxy-8-hydroxyguanosine 5'-triphosphate.

14. A kit for performing the method of claim 4, comprising said nucleoside triphosphate analogue means for replicating a template sequence so as to incorporate the nucleoside monophosphate portion of the nucleoside triphosphate analogue into non-identical copies of the template sequence, and instructions for use according to said method.

15. A kit according to claim 14, wherein the nucleoside triphosphate analogue is 6-(2-deoxy-β-D-erythropentofuranosyl)-3,4 dihydro-8H-pyrimido [4,5-c][1,2]oxazine-7-one 5'triphosphate.

16. A kit according to claim 14, further comprising wherein the means for replicating the template sequence comprises means for performing the polymerase chain reaction.

17. A kit according to claim 14, further comprising the four normal deoxynucleotides.

18. A kit according to claim 14, further comprising at least one member of the group consisting of 2'-deoxy-8-hydroxyguanosine 5'-triphosphate, 2-amino-9-(2-deoxy-β-D-erythropentofuranosyl)-6-methoxyaminopurine 5'-triphosphate, and $O^2$-ethylthymidine triphosphate.

* * * * *

SEQUENCE LISTING

<160> NUMBER OF SEQ ID NOS: 5

<210> SEQ ID NO 1
<211> LENGTH: 285
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Primer

<400> SEQUENCE: 1

```
gagtctggag gaggcttgat ccagcctggg gggtccctga gactctcctg tgcagcctct      60
gggttcaccg tcagtagcaa ctatatgagc tgggtccgcc aggctccagg gaaggggctg     120
gagtgggtct cagttattta tagcggtggt agcacatact acgcagactc cgtgaagggc     180
cgattcacca tctccagaga caattccaag aacacgctgt atctgcaaat gaacagcctg     240
agagctgagg acacggccgt gtattactgt gcaagaaagt ttcct                     285
```

<210> SEQ ID NO 2
<211> LENGTH: 95
<212> TYPE: PRT
<213> ORGANISM: Artificial Sequence
<220> FEATURE:
<223> OTHER INFORMATION: Description of Artificial Sequence: Primer
<220> FEATURE:
<223> OTHER INFORMATION: Primer

<400> SEQUENCE: 2

Glu Ser Gly Gly Gly Leu Ile Gln Pro Gly Gly Ser Leu Arg Leu Ser

-continued

```
                1               5                  10                 15

Cys Ala Ala Ser Gly Phe Thr Val Ser Ser Asn Tyr Met Ser Trp Val
                       20                  25                  30

Arg Gln Ala Pro Gly Lys Gly Leu Glu Trp Val Ser Val Ile Tyr Ser
                   35                  40                  45

Gly Gly Ser Thr Tyr Tyr Ala Asp Ser Val Lys Gly Arg Phe Thr Ile
               50                  55                  60

Ser Arg Asp Asn Ser Lys Asn Thr Leu Tyr Leu Gln Met Asn Ser Leu
        65                  70                  75                  80

Arg Ala Glu Asp Thr Ala Val Tyr Tyr Cys Ala Arg Lys Phe Pro
                       85                  90                  95
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Primer

<400> SEQUENCE: 3
ggccttgata ttcacaaacg aat                                      23

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Primer

<400> SEQUENCE: 4
tcttaccatt cgtttgtgaa tatcaaggcc                               30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Primer
<220> FEATURE:
<223> OTHER INFORMATION: Primer

<400> SEQUENCE: 5
tcttgccatt cgtttgtgaa tatcaaggcc                               30